United States Patent
Fujimoto et al.

(10) Patent No.: US 9,968,714 B2
(45) Date of Patent: *May 15, 2018

(54) BIODEGRADABLE ELASTOMERIC PATCH FOR TREATING CARDIAC OR CARDIOVASCULAR CONDITIONS

(71) Applicant: University of Pittsburgh—Of the Commonwealth System of Higher Education, Pittsburgh, PA (US)

(72) Inventors: Kazuro Lee Fujimoto, Pittsburgh, PA (US); Jianjun Guan, Pittsburgh, PA (US); Bradley B. Keller, Pittsburgh, PA (US); Kimimasa Tobita, Wexford, PA (US); William R. Wagner, Gibsonia, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/597,520

(22) Filed: Jan. 15, 2015

(65) Prior Publication Data
US 2015/0132251 A1    May 14, 2015

Related U.S. Application Data

(63) Continuation of application No. 11/823,359, filed on Jun. 27, 2007, now Pat. No. 8,974,542.

(Continued)

(51) Int. Cl.
*A61F 2/02* (2006.01)
*A61L 31/06* (2006.01)
(Continued)

(52) U.S. Cl.
CPC ........... *A61L 31/06* (2013.01); *A61K 9/0024* (2013.01); *A61K 9/7007* (2013.01)

(58) Field of Classification Search
CPC ... A61F 2/2481; A61K 9/0024; A61K 9/7007; A61L 31/06
See application file for complete search history.

(56) References Cited

U.S. PATENT DOCUMENTS

| 4,681,588 A | 7/1987 | Ketharanathan |
| 4,902,508 A | 2/1990 | Badylak et al. |

(Continued)

OTHER PUBLICATIONS

Guan J, Sacks MS, Beckman EJ, Wagner WR. Synthesis, characterization, and cytocompatibility of elastomeric, biodegradable poly(ester-urethane)ureas based on poly(caprolactone) and putrescine. J Biomed Mater Res. Sep. 5, 2002;61(3):493-503.

(Continued)

*Primary Examiner* — Corrine McDermott
*Assistant Examiner* — Christina Lauer
(74) *Attorney, Agent, or Firm* — The Webb Law Firm

(57) ABSTRACT

Provided herein is a biodegradable elastomeric patch that can be implanted on a heart or other portions of the cardiovascular system to repair tissue deficiencies or tissue damage. The biodegradable elastomeric patch may be engineered to have mechanical properties similar to that of soft tissue and to provide mechanical support to the damaged tissue. The biodegradable elastomeric patch also may comprise therapeutic agents to aid in the healing process. Methods also are provided for using a biodegradable elastomeric patch for treating patients suffering from tissue damage or tissue deficiencies in the cardiac or cardiovascular system.

23 Claims, 19 Drawing Sheets
(11 of 19 Drawing Sheet(s) Filed in Color)

Related U.S. Application Data

(60) Provisional application No. 60/805,980, filed on Jun. 27, 2006.

(51) Int. Cl.
*A61K 9/00* (2006.01)
*A61K 9/70* (2006.01)

(56) References Cited

U.S. PATENT DOCUMENTS

| | | | |
|---|---|---|---|
| 4,956,178 A | 9/1990 | Badylak et al. | |
| 5,053,228 A | 10/1991 | Mori et al. | |
| 5,100,422 A | 3/1992 | Berguer et al. | |
| 5,124,421 A | 6/1992 | Ulbrich et al. | |
| 5,171,262 A | 12/1992 | MacGregor | |
| 5,275,826 A | 1/1994 | Badylak et al. | |
| 5,281,422 A | 1/1994 | Badylak et al. | |
| 5,352,463 A | 10/1994 | Badylak et al. | |
| 5,372,821 A | 12/1994 | Badylak et al. | |
| 5,516,533 A | 5/1996 | Badylak et al. | |
| 5,554,389 A | 9/1996 | Badylak et al. | |
| 5,573,784 A | 11/1996 | Badylak et al. | |
| 5,610,241 A | 3/1997 | Lee et al. | |
| 5,645,860 A | 7/1997 | Knapp, Jr. et al. | |
| 5,702,717 A | 12/1997 | Cha et al. | |
| 5,711,969 A | 1/1998 | Patel et al. | |
| 5,753,267 A | 5/1998 | Badylak et al. | |
| 5,762,966 A | 6/1998 | Knapp, Jr. et al. | |
| 5,771,969 A | 6/1998 | Garay | |
| 5,807,581 A | 9/1998 | Rosenblatt et al. | |
| 5,866,414 A | 2/1999 | Badylak et al. | |
| 5,885,619 A | 3/1999 | Patel et al. | |
| 5,885,829 A * | 3/1999 | Mooney | A61L 27/3604 424/422 |
| 5,955,110 A | 9/1999 | Patel et al. | |
| 5,968,096 A | 10/1999 | Whitson et al. | |
| 6,030,634 A | 2/2000 | Wu et al. | |
| 6,099,567 A | 8/2000 | Badylak et al. | |
| 6,177,522 B1 * | 1/2001 | Brady | A61L 27/18 525/452 |
| 6,187,039 B1 | 2/2001 | Hiles et al. | |
| 6,458,889 B1 | 10/2002 | Trollsas et al. | |
| 6,485,723 B1 | 11/2002 | Badylak et al. | |
| 6,554,857 B1 | 4/2003 | Zilla et al. | |
| 6,576,265 B1 | 6/2003 | Spievack | |
| 6,579,538 B1 | 6/2003 | Spievack | |
| 6,651,672 B2 | 11/2003 | Roth | |
| 6,696,270 B2 | 2/2004 | Badylak et al. | |
| 6,783,776 B2 | 8/2004 | Spievack | |
| 6,793,939 B2 | 9/2004 | Badylak | |
| 6,833,408 B2 | 12/2004 | Sehl et al. | |
| 6,841,617 B2 | 1/2005 | Jeong et al. | |
| 6,849,273 B2 | 2/2005 | Spievack | |
| 6,852,339 B2 | 2/2005 | Spievack | |
| 6,861,074 B2 | 3/2005 | Spievack | |
| 6,887,495 B2 | 5/2005 | Spievack | |
| 6,890,562 B2 | 5/2005 | Spievack | |
| 6,890,563 B2 | 5/2005 | Spievack | |
| 6,890,564 B2 | 5/2005 | Spievack | |
| 6,893,431 B2 * | 5/2005 | Naimark | A61B 17/00234 604/891.1 |
| 6,893,666 B2 | 5/2005 | Spievack | |
| 7,067,121 B2 | 6/2006 | Mickle et al. | |
| 7,094,418 B2 | 8/2006 | Chudzik et al. | |
| 7,235,295 B2 | 6/2007 | Laurencin et al. | |
| 7,396,537 B1 | 7/2008 | Krupnick et al. | |
| 8,974,542 B2 * | 3/2015 | Fujimoto | A61K 9/0024 623/23.72 |
| 2002/0085994 A1 | 7/2002 | Ceres et al. | |
| 2002/0090725 A1 | 7/2002 | Simpson et al. | |
| 2002/0150622 A1 | 10/2002 | Philbrook et al. | |
| 2003/0092864 A1 * | 5/2003 | Gunatillake | C08G 18/4692 528/26 |
| 2003/0100944 A1 | 5/2003 | Laksin et al. | |
| 2004/0001892 A1 | 1/2004 | Healy et al. | |
| 2005/0013793 A1 * | 1/2005 | Beckman | C08G 18/12 424/78.27 |
| 2005/0238722 A1 | 10/2005 | Pathak et al. | |
| 2005/0260179 A1 | 11/2005 | Fishman et al. | |
| 2006/0025800 A1 * | 2/2006 | Suresh | A61B 17/0057 606/198 |
| 2006/0147433 A1 | 7/2006 | Hiles | |
| 2006/0177387 A1 * | 8/2006 | Slavin | A61K 35/28 424/50 |
| 2007/0014755 A1 | 1/2007 | Beckman et al. | |
| 2007/0014773 A1 | 1/2007 | Matheny et al. | |
| 2007/0014870 A1 | 1/2007 | Matheny | |
| 2007/0014871 A1 | 1/2007 | Matheny | |
| 2007/0014872 A1 | 1/2007 | Matheny et al. | |
| 2007/0014873 A1 | 1/2007 | Matheny | |
| 2007/0014874 A1 | 1/2007 | Matheny | |
| 2008/0096975 A1 | 4/2008 | Guan et al. | |
| 2008/0109070 A1 | 5/2008 | Wagner et al. | |
| 2008/0260831 A1 | 10/2008 | Badylak et al. | |
| 2008/0268019 A1 | 10/2008 | Badylak et al. | |

OTHER PUBLICATIONS

Guan J, Wagner WR. Synthesis, characterization and cytocompatibility of polyurethaneurea elastomers with designed elastase sensitivity. Biomacromolecules. Sep.-Oct. 2005;6(5):2833-42.

Gutowska A, Jeong B, Jasionowski M. Injectable gels for tissue engineering. Anat Rec. Aug. 1, 2001;263(4):342-9.

Hacking SA, Bobyn JD, Toh K, Tanzer M, Krygier JJ. Fibrous tissue ingrowth and attachment to porous tantalum. J Biomed Mater Res, 631-8 (52) 2000.

Han CK, Bae YH. Inverse thermally-reversible gelation of aqueous N-isopropylacrylamide copolymer solutions. Polymer. Jun. 1998;39(13):2809-14.

Healy KE, Rezania A, Stile RA. Designing biomaterials to direct biological responses. Ann N Y Acad Sci. Jun. 18, 1999;875:24-35.

Hennink WE, van Nostrum CF. Novel crosslinking methods to design hydrogels. Adv Drug Deliv Rev. Jan. 17, 2002;54(1):13-36.

Higuera CA, Inoue N, Lim JS, Zhang R, Dimaano N, Frassica FJ, Chao EY. Tendon reattachment to a metallic implant using an allogenic bone plate augmented with rhOP-1 vs. autogenous cancellous bone and marrow in a canine model. J Orthop Res. Sep. 2005;23(5):1091-9. Epub Apr. 7, 2005.

Hoerstrup SP, Ztind G, Sodian R, Schnell AM, Grtinenfelder J, Turina ML Tissue engineering of small caliber vascular grafts. Eur J Cardiothorac Surg. Jul. 2001;20(1):164-9.

Karlon WJ, Covell JW, McCulloch AD, Hunter JJ, Omens JH. Automated measurement of myofiber disarray in transgenic mice with ventricular expression of ras. Anat Rec. Dec. 1998;252(4):612-25.

Kim S, Chung EH, Gilbert M, Healy KE. Synthetic MMP-13 degradable ECMs based on poly(N-isopropylacrylamide-co-acrylicacid) semi-interpenetrating polymer networks. I. Degradation and cell migration. J Biomed Mater Res A. Oct. 1, 2005;75(1):73-88.

Kim S, Healy KE. Synthesis and characterization of injectable poly(N-isopropylacrylamide-co-acrylic acid) hydrogels with proteolytically degradable cross-links. Biomacromolecules. Sep.-Oct. 2003;4(5): 1214-23.

Lee BH, Vernon B. Copolymers of N-isopropylacrylamide, HEMA-lactate and acrylic acid with time-dependent lower critical solution temperature as a bioresorbable carrier. Polymer International. Feb. 2005;54(2):4 I 8-22.

Lee BH, Vernon B. In situ-gelling, erodible N-isopropylacrylamide copolymers. Macromol Biosci. Jul. 14, 2005;5(7):629-35.

Lee CH, Shin HJ, Cho IH, Kang YM, Kim IA, Park KD, Shin JW. Nanofiber alignment and direction of mechanical strain affect the ECM production of human ACL fibroblast.Biomaterials. Apr. 2005;26(11):1261-70.

Lehman GA. Injectable and bulk-forming agents for enhancing the lower esophageal sphincter. Am J Med. Aug. 18, 2003;115 Suppl 3A:188S-91S.

(56) References Cited

OTHER PUBLICATIONS

Li F, Carlsson D, Lohmann C, Suuronen E, Vascotto S, Kobuch K, Sheardown H, Munger R, Nakamura M, Griffith M. Cellular and nerve regeneration within a biosynthetic extracellular matrix forcorneal transplantation. Proc Natl Acad Sci U S A. Dec. 23, 2003;100(26):15346-51. Epub Dec. 5, 2003.

Li F, Griffith M, Li Z, Tanodekaew S, Sheardown H, Hakim M, Carlsson DJ. Recruitment of multiple cell lines by collagen-synthetic copolymer matrices in corneal regeneration.Biomaterials. Jun. 2005;26(16):3093-104.

Lightner DJ, Itano NB, Sweat SD, Chrouser KL, Fick F. Injectable agents: present and future. Curr Urol Rep. Oct. 2002;3(5):408-13.

Makino K, Hiyoshia J, Ohshima H. Kinetics of swelling and shrinking of poly (N-isopropylacrylamide) hydrogels at different temperatures. Colloids Surf B: Biointerfaces. Dec. 15, 2000;19(2):197-204.

Matsuda T, Ihara M, Inoguchi H, Kwon IK, Takamizawa K, Kidoaki S. Mechano-active scaffold design of small-diameter artificial graft made of electrospun segmented polyurethane fabrics. J Biomed Mater Res A. Apr. 1, 2005;73(1):125-31.

Matsumaru Y, Hyodo A, Nose T, Ito S, Hirano T, Ohashi S. Application of thermosensitive polymers as a new embolic material for intravascular neurosurgery. J Biomater Sci Polym Ed. 1996;7(9):795-804.

McMullen JR, Shioi T, Huang WY, Zhang L, Tarnavski 0, Bisping E, Schinke M, Kong S, Sherwood MC, Brown J, Riggi L, Kang PM, Izumo S. The insulin-like growth factor 1 receptor induces physiological heart growth via the phosphoinositide 3-kinase(pllOalpha) pathway. J Biol Chem. Feb. 6, 2004;279(6):4782-93. Epub Nov. 3, 2003.

Middleton JC, Tipton AJ. Synthetic Biodegradable Polymers as Medical Devices. Medical Plastics and Biomaterials Magazine. Medical Plastics and Biomaterials Magazine. Mar. 1998, p. 30. Available at: http://devicelink.com/mpb/archive/98/03/002.html.

Nancollas H. In vitro studies of calcium phosphate crystallization. In: Mann S, Webb J, Williams RPJ, eds. Biomineralization: Chemical and biochemical perspectives. New York: VCH, 1989, pp. 157-182.

Nedovic VA, Obradovic B, Poncelet D, Goosen MFA, Leskosek-Cukalovic 0, Bugarski B. Cell immobilization by electrostatic droplet generation. Landbauforsch Volk. 2002;241:11-7.

Neradovic D, Hinrichs WLJ, Kettenes-van den Bosch JJ, Hennink WE. Poly(N-isopropylacrylamide) with hydrolyzable lactic acid ester side groups: a new type of thermosensitive polymer. Macromolecular Rapid Comm. Oct. 1999;20(11):577-81.

Ohya S, Matsuda T. Poly(N-isopropylacrylamide) (PNIPAM)-grafted gelatin as thermoresponsivethree-dimensional artificial extracellular matrix: molecular and formulation parameters vs. cell proliferation potential. J Biomater Sci Polym Ed. 2005;16(7):809-27.

Ohya S, Nakayama Y, Matsuda T. Thermoresponsive artificial extracellular matrix for tissue engineering:hyaluronic acid bioconjugated with poly(N-isopropylacrylamide) grafts. Biomacromolecules. 2001 Fall;2(3):856-63.

Opitz F, Schenke-Layland K, Richter W, Martin DP, Degenkolbe I, Wahlers T,Stock UA. Tissue engineering of ovine aortic blood vessel substitutes using applied shearstress and enzymatically derived vascular smooth muscle cells. Ann Biomed Eng. Feb. 2004;32(2):212-22.

Ota T, Sawa Y, Iwai S, Kitajima T, Ueda Y, Coppin C, Matsuda H, Okita Y. Fibronectin-hepatocyte growth factor enhances reendothelialization in tissue-engineered heart valve. Ann Thorac Surg. Nov. 2005;80(5):1794-801.

Radisic M, Yang L, Boublik J, Cohen RJ, Langer R, Freed LE, Vunjak-Novakovic G. Medium perfusion enables engineering of compact and contractile cardiac tissue. Am J Physiol Heart Circ Physiol. Feb. 2004;286(2):H507-16. Epub Oct. 9, 2003.

Ray JL, Leach R, Herbert JM, Benson M. Isolation of vascular smooth muscle cells from a single murine aorta. Methods Cell Sci. 2001;23(4): 185-8.

Reddy GK, Enwemeka CS. A simplified method for the analysis of hydroxyproline in biological tissues. Clin Biochem. Jun. 1996;29(3):225-9.

Riboldi SA, Sampaolesi M, Neuenschwander P, Cossu G, Mantero S. Electrospun degradable polyesterurethane membranes: potential scaffolds for skeletal muscle tissue engineering.Biomaterials. Aug. 2005;26(22):4606-15. Epub Jan. 7, 2005.

Rimsay R, Robinson JJ. Biochemical Analysis of Hyaline Gelation: An Essential Step in the Assembly of the Sea Urchin Extraembryonic Matrix, the Hyaline Layer. Archives of Biochemistry and Biophysics. 2003; (414): 279-286.

Ringel RL, Kahane JC, Hillsamer PJ, Lee AS, Badylak SF. The application of tissue engineering procedures to repair the larynx. J Speech Lang Hear Res. Feb. 2006;49(1):194-208.

Robinson JJ. Roles for Ca2+, Mg2+ and NaCl in modulating the self-association reaction of hyalin, a major protein component of the sea-urchin extraembryonic hyaline layer. Biochem J. Nov. 15, 1988;256(1):225-8.

Robinson KA, Li J, Mathison M, Redkar A, Cui J, Chronos NA, Matheny RG, Badylak SF. Extracellular matrix scaffold for cardiac repair. Circulation. Aug. 30, 2005; 112(9 Suppl):I135-43.

Ross RS, Borg TK. Integrins and the myocardium. Circ Res. Jun. 8, 2001;88(11): 1112-9.

Sacks MS. Biaxial mechanical evaluation of planar biological materials. J Elasticity 2000; 61(1-3): 199-246.

Santucci RA, Barber TD. Resorbable extracellular matrix grafts in urologic reconstruction.Int Braz J Urol. May-Jun. 2005;31(3):192-203. Review. Erratum in: Int Braz J Urol. Jul.-Aug. 2005;31(4):414.

Sarikaya A, Record R, Wu CC, Tullius B, Badylak S, Ladisch M. Antimicrobial activity associated with extracellular matrices. Tissue Eng. Feb. 2002;8(1):63-71.

Schmedlen RH, Masters KS, West JL. Photocrosslinkable polyvinyl alcohol hydrogels that can be modified with celladhesion peptides for use in tissue engineering. Biomaterials. Nov. 2002;23(22):4325-32.

Schmolka IR. Artificial skin. I. Preparation and properties of pluronic F-127 gels for treatment of burns. J Biomed Mater Res. Nov. 1972;6(6):571-82.

Shimizu T, Yamato M, Isoi Y, Akutsu T, Setomaru T, Abe K, Kikuchi A, Umezu M, OkanoT. Fabrication of pulsatile cardiac tissue grafts using a novel 3-dimensional cellsheet manipulation technique and temperature-responsive cell culture surfaces. Circ Res. Feb. 22, 2002;90(3):e40-48.

Stankus JJ, Guan J, Fujimoto K, Wagner WR. Microintegrating smooth muscle cells into a biodegradable, elastomeric fiber matrix. Biomaterials. Feb. 2006;27(5):735-44. Epub Aug. 10, 2005.

Stankus JJ, Guan J, Wagner WR. Fabrication of biodegradable elastomeric scaffolds with sub-micron morphologies. J Biomed Mater Res A. Sep. 15, 2004;70(4):603-14.

Stankus JJ, Soletti L, Fujimoto K, Hong Y, Vorp DA, Wagner WR. Fabrication of cell microintegrated blood vessel constructs through electrohydrodynamic atomization.Biomaterials. Jun. 2007;28(17):2738-46. Epub Feb. 20, 2007.

Stankus JJ. Functional Elastomeric Scaffold Development for Tissue Engineering. Ph.D. Dissertation, University of Pittsburgh, 2006.

Stile RA, Healy KE. Thermo-responsive peptide-modified hydrogels for tissue regeneration. Biomacromolecules. 2001 Spring;2(1):185-94.

Taipale J, Keski-Oja J. Growth factors in the extracellular matrix. FASEB J. Jan. 1997;II(I):51-9.

Temple MD, Bashari E, Lu J, Zong WX, Thompson CB, Pinto NJ, Monohar SK, King RCY, MacDiarmid AG. Electrostatic transportation of living cells through air. Abstracts of Papers, 223 ACS National Meeting, Orlando, FL, Apr. 7-11, 2002.

Tiwari A, Salacinski HJ, Punshon G, Hamilton G, Seifalian AM. Development of a hybrid cardiovascular graft using a tissue engineering approach. FASEB J. Jun. 2002;I6(8):791-6.

van Dijk-Wolthuis WNE, Tsang SKY, Kettenes-van den Bosch JJ, Hennink WE. A new class of polymerizable dextrans with hydrolyzable groups: hydroxyethyl methacrylated dextran with and without oligolactate spacer. Polymer. Dec. 1997;38(25):6235-42.

(56) References Cited

OTHER PUBLICATIONS

Veazey WS, Anusavice KJ, Moore K. Mammalian cell delivery via aerosol deposition. JBiomed Mater Res B Appl Biomater. Feb. 15, 2005;72(2):334-8.
Venere E. New materials hold promise for human healing applications. Purdue News, Mar. 22, 2001.
Vihola H, Laukkanen A, Valtola L, Tenhu H, Hirvonen J. Cytotoxicity of thermosensitive polymers poly(N-isopropylacrylamide) ,poly(N-vinylcaprolactam) and amphiphilically modified poly(N-vinylcaprolactam). Biomaterials. Jun. 2005;26(16):3055-64.
Williams BR, Gelman RA, Poppke DC, Piez KA. Collagen fibril formation. Optimal in vitro conditions and preliminary kinetic results. J Biol Chem. Sep. 25, 1978;253(18):6578-85.
Wood JD, Simmons-Byrd A, Spievack AR, Badylak SF. Use of a particulate extracellular matrix bioscaffold for treatment of acquired urinary incontinence in dogs. J Am Vet Med Assoc. Apr. 1, 2005;226(7):1095-7.
Wright Medical Technology. Comparative analysis: GRAFTJACKET™ Periosteum Replacement Scaffold & SIS™ Porcine Small Intestine Submucosa. Copyright in 2002.
Xu CY, Inai R, Kotaki M, Ramakrishna S. Aligned biodegradable nanofibrous structure: a potential scaffold for blood vessel engineering. Biomaterials. Feb. 2004;25(5):877-86.
Xu JW, Zaporojan V, Peretti GM, Roses RE, Morse KB, Roy AK, Mesa JM, Randolph MA, Bonassar LJ, Yaremchuk MJ. Injectable tissue-engineered cartilage with different chondrocyte sources. Plast Reconstr Surg. Apr. 15, 2004;113(5):1361-71.
Zantop T, Gilbert TW, Yoder MC, Badylak SF. Extracellular matrix scaffolds are repopulated, in part, by bone marrow-derived cells in a mouse model of achilles tendon reconstruction. J Orthop Res. Jun. 2006;24(6):1299-309.
Zhang P, Zhang H, Wang H, Wei Y, Hu S. Artificial matrix helps neonatal cardiomyocytes restore injured myocardium in rats. Artif Organs. Feb. 2006;30(2):86-93.
Au A, Ha J, Polotsky A, Krzyminski K, Gutowska A, Hungerford DS, Frondoza CG. Thermally reversible polymer gel for chondrocyte culture, J Biomed Mater Res A. Dec. 15, 2003, 67(4): 1310-9.
Badylak S, Arnoczky S, Plouhar P, Haut R, Mendenhall V, Clarke R, Horvath C. Naturally occurring extracellular matrix as a scaffold for musculoskeletal repair. Clin Orthop Relat Res. Oct. 1999(367 Suppl):S333-43.
Badylak S, Meuring S, Chen M, Spievack A, Simmons-Byrd A. Resorbable bioscaffold for esophageal repair in a dog model. J Pediatr Surg. Jul. 2000;35(7):1097-103.
Badylak S, Obermiller J, Geddes L, Matheny R. Extracellular matrix for myocardial repair. Heart Surg Forum. 2003;6(2):E20-6.
Badylak SF, Kochupura PV, Cohen IS, Doronin SV, Saltman AE, Gilbert TW, Kelly DJ, Ignotz RA, Gaudette GR. The use of extracellular matrix as an inductive scaffold for the partial replacement of functional myocardium. Cell Transplant. 2006;15 Suppl I:S29-40.
Badylak SF, Tullius R, Kokini K, Shelbourne KD, Klootwyk T, Voytik SL, Kraine MR, Simmons C. The use of xenogeneic small intestinal submucosa as a biomaterial for Achilles tendon repair in a dog model. J Biomed Mater Res. Aug. 1995;29(8):977-85.
Badylak SF, Vorp DA, Spievack AR, Simmons-Byrd A, Hanke J, Freytes DO, Thapa A, Gilbert TW, Nieponice A. Esophageal reconstruction with ECM and muscle tissue in a dog model. J Surg Res. Sep. 2005;128(1):87-97.
Badylak. The extracellular matrix as a scaffold for tissue reconstruction. Semin Cell Dev Biol. Oct. 2002;13(5):377-83.
Badylak. Xenogeneic extracellular matrix as a scaffold for tissue reconstruction. Transpl Immunol. Apr. 2004;I2(3-4):367-77.
Bernacca GM, Mackay TG, Gulbransen MJ, Donn AW, Wheatley DJ. Polyurethane heart valve durability: effects of leaflet thickness and material. Int J Artif Organs. Jun. 1997;20(6):327-31.
Billiar KL, Sacks MS. Biaxial mechanical properties of the natural and glutaraldehyde treated aortic valve cusp—Part I: Experimental results. J Biomech Eng. Feb. 2000;I22(1):23-30.
Brightman AO, Rajwa BP, Sturgis JE, McCallister ME, Robinson JP, Voytik-Harbin SL. Time-Lapse Confocal Reflection Microscopy of Collagen Fibrillogenesis and Extracellular Matrix Assembly In Vitro. Biopolymers. Sep. 2000;54(3): 222-34.
Bromberg LE, Ron ES. Temperature-responsive gels and thermogelling polymer matrices for protein and peptide delivery. Adv Drug Deliv Rev. May 4, 1998;31(3):197-221.
Cao YL, Ibarra C, Vacanti C. Preparation and use of thermosensitive polymers. In: Morgan JR, Yarmush ML, eds. Methods in Molecular Medicine: Tissue engineering Methods and Protocols. Totowa, N.J.; Humana Press, 1999, pp. 75-84.
Chaudhuri BB, Kundu P, Sarkar N. Detection and gradation of oriented texture. Pattern Recogn Lett. 1993;14 (2):147-53.
Cho JH, Kim SH, Park KD, Jung MC, Yang WI, Han SW, Noh JY, Lee JW. Chondrogenic differentiation of human mesenchymal stem cells using a thermosensitive poly(N-isopropylacrylamide) and water-soluble chitosan copolymer. Biomaterials. Nov. 2004;25(26):5743-51.
Corda S, Samuel JL, Rappaport L. Extracellular matrix and growth factors during heart growth. Heart Fail Rev. Jun. 2000;5(2):119-30.
Courtney T, Liao J, Sacks MS, Stankus J, Guan J, Wagner W. Meso- and micromechanics of elastomeric electrospun PEUU scaffolds for cardiovascular tissue engineering. Regenerate World Congress on Tissue Engineering and Regenerative Medicine, Apr. 25-27, 2006, Pittsburgh, PA. Published on CD, Conference Proceedings Regenerate World Congress on Tissue Engineering and Regenerative Medicine, Abstract # 572.
Courtney T, Liao J, Sacks MS, Stankus J, Guan J, Wagner W. Micromechanics of electrospun polyester urethane urea scaffolds. Society for Biomaterials 2006 Ann ual Meeting, Apr. 26-29, 2006, Pittsburgh, PA. Published on CD, Transactions of the 31st Annual Meeting of the Society for Biomaterials, vol. XXIX, Abstract # 163.
Courtney T, Liao J, Stankus J, Guan J, Wagner W, Sacks MS. Micromechanics of electrospu n poly ester urethane urea scaffolds for soft tissue engineering. Fifth World Congress of Biomechanics, Jul. 29-Aug. 4, 2006, Munich, Germany. Published in Journal of Biomechanics 2006 39(Supp 1): S262.
Courtney T, Sacks MS, Liao J , Stankus J, Guan J, Wagner W. Incorporation of fiber tortuosity effects in a constitutive model for scaffolds. ASME 2006 Summer Bioengineering Conference, Jun. 21-25, 2006, Amelia Island, Florida. Published on CD, Proceedings of the 2006 Summer Bioengineering Conference, Abstract # BI02005-157686.
Courtney T, Sacks MS, Stankus J, Guan J, Wagner WR. Analysis and design of novel electrospun PEU LT scaffolds for soft tissue engineering. 2005 Annual Fall Mtg, Nov. 28-Dec. 1, 2005, Boston, MA. Abstract LI3.I.
Courtney T, Sacks MS, Stankus J, Guan J, Wagner WR. Design and analysis of tissue engineering scaffolds that mimic soft tissue mechanical anisotropy. Biomaterials. Jul. 2006;27(19):3631-8. Epub Mar. 20, 2006.
Courtney TD, Sacks MS, Stankus JJ, Guan J , Wagner WR. Analysis and design of novel electrospun PEUU scaffolds for soft tissue engineering. The 8th Annual Meeting of the Tissue Engineering Society International, Oct. 22-25, 2005, Shanghai, P.R. China. Published on CD, Final Program and Abstract Book TESI 2005, Abstract # 193.
Courtney TD, Sacks MS, Stankus JJ, Guan J , Wagner WR. Structural and mechanical characterization of poly( ester urethane) elastomeric scaffolds for cardiovascular soft tissue engineering. Society for Biomaterials 30th Annual Meeting, Memphis, TN, Apr. 27-30, 2005. Published on CD, Transactions of the 30th Annual Meeting:H.
Courtney TD, Sacks MS, Stankus JJ, Guan J, Wagner WR. Analysis and design of novel electrospun PEUU scaffolds for soft tissue engineering. ASME 2005 Summer Bioengineering Conference, V ail, CO, Jun. 22-26, 2005. Published on CD, Proceedings of the 2005 Summer Bioengineering Conference Vail Cascade Resort and Spa, Vail, CO; Abstract # b0241329.
Cushing MC, Liao JT, Anseth KS. Activation of valvular interstitial cells is mediated by transforming growth factor-beta1 interactions with matrix molecules. Matrix Biol. Sep. 2005;24(6):428-37.

(56) References Cited

OTHER PUBLICATIONS de la Fuente SG, Gottfried MR, Lawson DC, Harris MB, Mantyh CR, Pappas TN. Evaluation of porcine-derived small intestine submucosa as a biodegradable graft for gastrointestinal healing. J Gastrointest Surg. 96-101 (7) 2003.

Dedecker F, Grynberg M, Staerman F. Small intestinal submucosa (SIS): prospects in urogenital surgery. Prog Urol. Jun. 2005;15(3):405-10. (abstract).

Deglau TE, Litwak K, Villanueva FS, Wagner WR. Surface modification of vascular tissue for targeted delivery of endothelial cells and microspheres. Abstract for Biomedical Engineering Society 2000 Annual Fall Meeting, Oct. 12-14, 2000. Ann Biomed Eng. 2000;28(Supplement):S-23.

Dejardin LM, Arnoczky SP, Ewers BJ, Haut RC, Clarke RB. Tissue-engineered rotator cuff tendon using porcine small intestine submucosa. Histologic and mechanical evaluation in dogs. AJSM. 2001;29:175-84.

Drury JL, Mooney DJ. Hydrogels for tissue engineering: scaffold design variables and applications. Biomaterials. Nov. 2003; 24(24):4337-51.

Duruisseau 0, Wagner I, Fugain C, Chabolle F. Endoscopic rehabilitation of vocal cord paralysis with a silicone elastomer suspension implant. Otolaryngol Head Neck Surg. Sep. 2004;131(3):241-7.

Elbjeirami WM, Yonter EO, Starcher BC, West JL. Enhancing mechanical properties of tissue-engineered constructs via lysyl oxidase crosslinking activity. J Biomed Mater Res A. Sep. 1, 2003;66(3):513-21.

Feil H, Bae TH, Feijen J, Kim SW. Effect of comonomer hydrophilicity and ionization on the lower critical solution temperature of N-isopropylacrylamide copolymers. Macromolecules. 1993;26(10);2496-2500.

Freytes DO, Badylak SF, Webster TJ, Geddes LA, Rundell AE. Biaxial strength of multilaminated extracellular matrix scaffolds. Biomaterials. 2004;25(12):2353-61.

Freytes, DO, Lee AS, Badylak SF. Porcine Urinary Bladder Matrix Derived Gel for Tissue Engineering Applications. Regenerate World Congress and Society for Biomaterials, Pittsburgh, PA, 2006. (abstract).

Freytes, DO, Lee AS, Badylak SF. Porcine Urinary Bladder Matrix Derived Gel for Tissue Engineering Applications. Regenerate World Congress and Society for Biomaterials, Pittsburgh, PA, 2006. (poster).

Fujimoto KL, Tobita K, Merryman DW, Momoi N, Guan J, Keller BB, Sacks M, Wagner WR. Elastic, biodegradable cardiac patch induces contractile smooth muscle bundles in sub-acute myocardial infarction, improving cardiac remodeling and function. World Congress of Tissue Engineering, Pittsburgh, PA 2006.

Fujimoto KL, Tobita K, Momoi N, Keller BB, Guan JJ, Wagner WR. Elastic, biodegradable cardiac patch induces contractile smooth muscle bundles in sub-acute myocardial infarction, improving cardiac remodeling and function. AHA meeting, Dallas TX, 2005.

Gelman RA, Williams BR, Piez KA. Collagen fibril formation. Evidence for a multistep process. J Biol Chem. Jan. 10, 1979;254(1):180-6.

Gilbert TW, Freytes DO, Badylak SF, Chou CP, Doorley G, Simone M, Walker N, Piehler HR. Development of a Hybrid ECM/Porous Metal Scaffold for Connective Tissue Ingrowth. Regenerate World Congress Meeting: Apr. 2006. Pittsburgh, PA. (Abstract).

Gilbert TW, Freytes DO, Badylak SF, Chou CP, Doorley G, Simone M, Walker N, Piehler HR. Development of a Hybrid ECM/Porous Metal Scaffold for Connective Tissue Ingrowth. Regenerate World Congress Meeting: Apr. 2006. Pittsburgh, PA. (poster).

Gotlieb AI, Rosenthal A, Kazemian P. Fibroblast growth factor 2 regulation of mitral valve interstitial cell repair in vitro. J Thorac Cardiovasc Surg. Sep. 2002;124(3):591-7.

Grashow JS, Yoganathan AP, Sacks MS. Biaixal stress-stretch behavior of the mitral valve anterior leaflet at physiologic strain rates. Ann Biomed Eng. Feb. 2006;34(2):315-25. Epub Feb. 1, 2006.

Guan et al. "Preparation and characterization of highly porous, biodegradable polyurethane scaffolds for soft tissue applications"; Science Direct; Dec. 8, 2004; pp. 3961-3971.

Guan et al. Synthesis, characterization, and cytocompatibility of elastomeric, biodegradable poly(ester-urethane)ureas based on poly(caprolactone) and putrescine; Wiley InterScience; May 17, 2002; pp. 493-503.

Guan J, Fujimoto KL, Sacks MS, Wagner WR. Preparation and characterization of highly porous, biodegradable polyurethane scaffolds for soft tissue applications. Biomaterials. Jun. 2005;26(18):3961-71.

Guan J, Sacks MS, Beckman EJ, Wagner WR. Biodegradable poly( ether ester urethane)urea elastomers based on poly(ether ester) triblock copolymers and putrescine: synthesis, characterization and cytocompatibility. Biomaterials. Jan. 2004;25(1):85-96.

\* cited by examiner

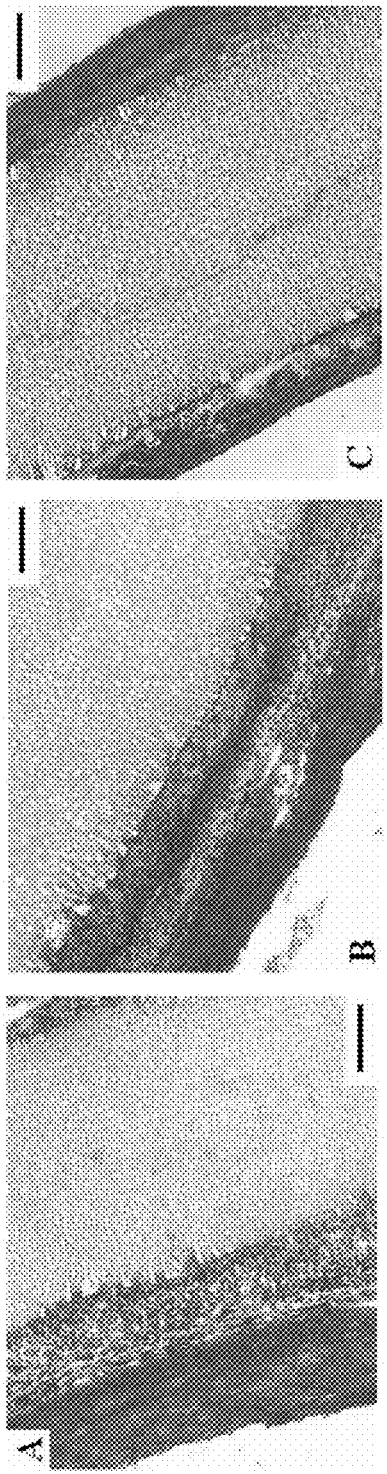

BIODEGRADABLE ELASTOMERIC PATCH FOR TREATING CARDIAC OR CARDIOVASCULAR CONDITIONS

CROSS REFERENCE TO RELATED APPLICATIONS

This application is a Continuation of U.S. patent application Ser. No. 11/823,359, filed Jun. 27, 2007, now U.S. Pat. No. 8,974,542, which claims the benefit under 35 U.S.C. § 119(e) to U.S. Provisional Patent Application No. 60/805,980, filed on Jun. 27, 2006, each of which is incorporated herein by reference in its entirety.

STATEMENT REGARDING FEDERAL FUNDING

This invention was made with government support under Grant Number HL069368 awarded by the National Institutes of Health. The government has certain rights to the invention.

Provided herein are medical devices, and in particular, biodegradable elastomeric patches that can be implanted on the heart or portions of the cardiovascular system to treat a variety of cardiac or cardiovascular conditions. Also provided herein are methods of treating a patient suffering from cardiac or cardiovascular conditions by implanting biodegradable elastomeric patches.

Either disease or injury may cause heart muscle to have insufficient strength or function. For example, a myocardial infarction induces loss of contractile mass and formation of scar tissue in heart (FIG. 1). Chronic heart failure following a large myocardial infarction is a serious and progressive disease whereby the hemodynamic status of the affected patient worsens over time despite the absence of clinically apparent adverse intercurrent events. This deterioration is accompanied by progressive left ventricular chamber remodeling. At the cellular level, this undesirable remodeling process is characterized by loss of functional cardiac units, myocyte hypertrophy and interstitial fibrosis. At the macroscopic level, the remodeling process is characterized by changes in left ventricular size and shape. Among clinical indicators of progressive left ventricular remodeling, left ventricular dilation and increased left ventricular sphericity are sensitive predictors of poor long-term outcome and harbingers of death.

Medical therapies, such as angiotensin converting enzyme (ACE) inhibitors and/or β-blockers, improve survival in chronic heart failure. Many treatments have been proposed for surgical repair of left ventricular aneurysms, including traditional linear closure techniques and endoventricular circular patch plasty. These surgeries increase ventricular systolic function by normalizing left ventricular chamber size and shape. However, in the long-term, unwanted chamber re-dilation and decompensation are still a concern.

Other surgical procedures for treating post-infarct left ventricular deterioration have been reported However, the non-biodegradable materials used in many of these procedures are left permanently in the body, which increases the risk of late infection, calcification and/or subsequent materials-related failures. Thus, the long-term outlook for many patients following myocardial infarction is bleak. Such patients account for approximately half of the candidates for heart transplantation.

Similar problems are faced by individuals suffering from tissue deficiencies in the cardiac or cardiovascular system as a result of congenital conditions. Often, the reconstructive surgeries used to repair these tissue deficiencies involve the implantation of synthetic or xenotypic material such as poly(ethylene terephthalate) fabric (Dacron®), expanded poly(tetrafluoro ethylene) (ePTFE), or glutaraldehyde-fixed bovine pericardium. The limitations of such materials are well known. The implant becomes a permanent foreign body that has the potential to serve as a nidus for infection, and in constrained geometries this foreign body will prevent desirable tissue growth and remodeling. It is notable that the primary polymeric materials used in reconstructive procedures, poly(ethylene terephthalate) (PET, Dacron®) and ePTFE, are polymers developed for a broad array of commercial applications prior to adoption by the medical community. It would be desirable to develop biologically compatible materials that can be specifically used to treat individuals suffering from cardiac or cardiovascular conditions involving tissue deficiency or injury.

SUMMARY

Provided are medical devices and related methods that are useful for enhancing or maintaining cardiac or cardiovascular function due to disease or injury. The medical device may be a biodegradable elastomeric patch capable of providing mechanical support as well as encouraging tissue growth or cell survival. The elastomeric patch may also comprise drugs or cells, which also contribute to providing therapeutic or prophylactic treatments.

Also provided is a method for treating a cardiac or cardiovascular condition. The method comprises implanting a biodegradable, elastomeric patch at or adjacent to the tissue damage or defect. In one non-limiting embodiment, the damage or defect is in a left ventricular region of a heart which can result from a myocardial infarction. The damage or defect in the cardiac or cardiovascular tissue may be a deficiency resulting from a congenital defect. The damage or defect in the cardiac or cardiovascular tissue also may be in a right ventricular outflow tract of a heart or in a heart valve.

In one non-limiting embodiment of the device and method, the biodegradable elastomeric patch comprises a polymer composition comprising one or both of a poly(ester urethane) urea elastomer or a poly(ether ester urethane) urea elastomer. The elastomer may comprise a diamine, such as putrescine or lysine ethyl ester or a polycaprolactone, such as a polycaprolactone diol. In one non-limiting embodiment, the elastomer may comprise a triblock copolymer comprising a polycaprolactone, such as a polycaprolactone-b-polyethylene glycol-b-polycaprolactone triblock copolymer. In another non-limiting embodiment, the polymer composition is functionalized with an adhesion-promoting peptide, such as RGD. The composition can be porous, for example and without limitation, the polymer composition may have a porosity of approximately 85%.

In one non-limiting embodiment, the elastomer comprises an isocyanate derivative, a polycaprolactone diol, and a diamine chain extender. In one embodiment thereof, the ratio of isocyanate derivative:polycaprolactone diol:diamine chain extender is 2:1:1. In yet another non-limiting embodiment, the elastomer comprises an isocyanate derivative, a triblock copolymer comprising polycaprolactone, and a diamine chain extender. In one example thereof, the ratio of isocyanate derivative:triblock copolymer:diamine chain extender is 2:1:1.

The device optionally may further comprise a therapeutic agent, such as, without limitation one or more of basic fibroblast growth factor (bFGF), acidic fibroblast growth factor (aFGF), vascular endothelial growth factor (VEGF), pleiotrophin protein, midkine protein, anti-inflammatories, and anti-clotting agents.

The device optionally may further comprise cells that optionally release a therapeutic agent. The therapeutic agent may be covalently linked to a polymer in the polymer composition and is released during degradation of the patch. In one non-limiting example, the therapeutic agent is putresceine that is covalently linked to the polymer. The cells may be stem cells, precursor stem cells, smooth muscle cells, skeletal myoblasts, myocardial cells, endothelial cells, and genetically modified cells.

The biodegradable elastomeric patch may be prepared by any useful method, such as by electrospinning, thermally induced phase separation or by solvent casting/salt leaching. Also provided is a method of making a patch or device as described herein by electrospinning, thermally induced phase separation or by solvent casting/salt leaching.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A shows a photograph of the anterior view of a heart in the control group. S denotes the control scar. FIG. 2B shows a photograph of the anterior view of a heart in the test group. P denotes the patch, where the black arrows point to the approximate perimeter of the patch. FIG. 2C shows a photograph of the cross-sectional view of the left ventricular wall in the control group. FIG. 2D shows a photograph of the cross-sectional view of the left ventricular wall in the test group. The white arrows indicate the infarcted anterior wall. Scale bars: 5 mm.

FIG. 3A shows H&E-stained tissue for the control group. FIG. 3B shows H&E-stained tissue for the PEUU patched group. FIG. 3C shows a higher resolution photomicrograph of H&E-stained tissue for the control group. At the same location as FIG. 3C, FIG. 3D shows a photomicrograph of immunohistochemically-stained tissue for α-smooth muscle actin (green) and for nuclei (blue). FIG. 3E shows a higher resolution photomicrograph of H&E-stained tissue for the PEUU patched group. At the same location as FIG. 3E, FIG. 3F shows a photomicrograph for immunohistochemically-stained tissue for α-smooth muscle actin (green) and for nuclei (blue). Scale bars for FIGS. 3A-3B are 500 μm and scale bars for FIG. 3C-3F are 200 μm.

FIG. 4A shows photomicrographs of tissue stained for alpha-smooth muscle actin (α-SMA), for caldesmon and a merged photomicrograph showing both stains. FIG. 4B shows photomicrographs of tissue stained for alpha-smooth muscle actin (α-SMA), for calponin and a merged photomicrograph showing both stains. FIG. 4C shows photomicrographs of tissue stained for alpha-smooth muscle actin (α-SMA), for SM 22α and a merged photomicrograph showing both stains. FIG. 4C shows photomicrographs of tissue stained for alpha-smooth muscle actin (α-SMA), for smooth muscle myosin heavy chain 2 (SMMHC-II) and a merged photomicrograph showing both stains. Scale bars are 20 μm.

FIG. 5A shows the structural features typical of mature contractile phenotype smooth muscle cells, where My denotes myofibril and N denotes nuclear. FIGS. 5B and 5C show higher resolution images, where white arrows indicate caveole and black arrows indicate dense bodies. Scale bars are 2 μm in FIG. 5A and 100 nm in FIG. 5B-5C.

FIG. 7A is a schematic showing the left parasternal long axis view and short axis view of the heart. FIG. 7B is an echocardiogram of the long axis view. FIG. 7C is an echocardiogram of the short axis view.

FIG. 8A is an echocardiogram, where the EDA is traced in a white line. FIG. 8B is a graph showing the percentage change in EDA from implantation day (0 wk). Data is shown for the PEUU patched group ("patch") and the control group ("sham") for the time points of implantation day (0 wk), four weeks after implantation (4 wk), and eight weeks after implantation (8 wk).

FIG. 9A is a graph showing the end-diastolic area for the time points of preimplantation (Pre), four weeks after implantation (4 w), and eight weeks after implantation (8 w). FIG. 9B is a graph showing the fractional area change for the same time points. Data is shown for the PEUU patch group (filled circles) and the control group (empty circles). Each symbol denotes the mean value and the error bars refer to the standard deviation of the value. Two-factor repeated ANOVA was performed to obtain statistic error analysis, where "★" refers to P<0.05 between groups indicated by the bracket and "†" refers to P<0.05 between that data and the preimplantation data within the group.

FIG. 10A is a graph of the circumferential strain and FIG. 10B is a graph of the longitudinal strain. Data is shown for the normal group without an induced infarct (filled circles), the control group with an induced infarct but no patch (empty circles), and the PEUU patch group with an induced infarct and a patch (filled triangles).

FIG. 11A shows the PEUU scaffold surface, where the scale bar is 50 μm. FIG. 11B shows the cross-section of the PEUU scaffold, where the scale bar is 100 μm. FIG. 11C is a photograph of the punched 6 mm diameter PEUU patch.

FIG. 12A is a photograph of the heart in the location with the implanted PEUU patch. FIG. 12B is a photograph of the heart in the location with the ePTFE implant. Scale bar is 5 mm.

FIG. 13A is a photomicrograph showing H&E-staining of the transition region between the PEUU patch and native tissue. FIG. 13B is photomicrograph showing H&E-staining of the transition region between the ePTFE implant and native tissue. Black arrows indicate implanted material edge. "c" denotes microvasculature. Scale bar is 20 µm.

FIGS. 14A-14C are photomicrographs taken after implanting an ePTFE implant, where images are shown for four weeks (A), eight weeks (B) and twelve weeks (C) after implantation. FIGS. 14D-14F are photomicrographs taken after implanting a PEUU patch, where images are shown for four weeks (D), eight weeks (E) and twelve weeks (F) after implantation. Scale bars are 100 µm. The right ventricular cavity is to the left or lower left for all photomicrographs.

FIGS. 15A-15F are photomicrographs of Masson trichrome-stained cardiac tissue at different times after an implant in the free wall of the right ventricle. FIGS. 15A-15C are photomicrographs after implanting an ePTFE implant. Photomicrographs are shown for four weeks (A), eight weeks (B) and twelve weeks (C) after implantation. FIGS. 15D-15F are photomicrographs taken after implanting a PEUU patch, where photomicrographs are shown for four weeks (D), eight weeks (E) and twelve weeks (F) after implantation. Stains indicate collagen (blue), fibrous cells (red), and nuclei (black). Scale bars are 100 µm.

FIG. 16A shown H&E-stained tissue and FIG. 16B show immunohistochemically-stained tissue after an ePTFE implant. FIG. 16C shows H&E-stained tissue and FIG. 16D shows an immunohistochemically-stained tissue after implantation of a PEUU patch. Stains indicate vWF (endothelial cells (red)) and nuclei (blue). Scale bars are 100 µm.

DETAILED DESCRIPTION

Figure 1:
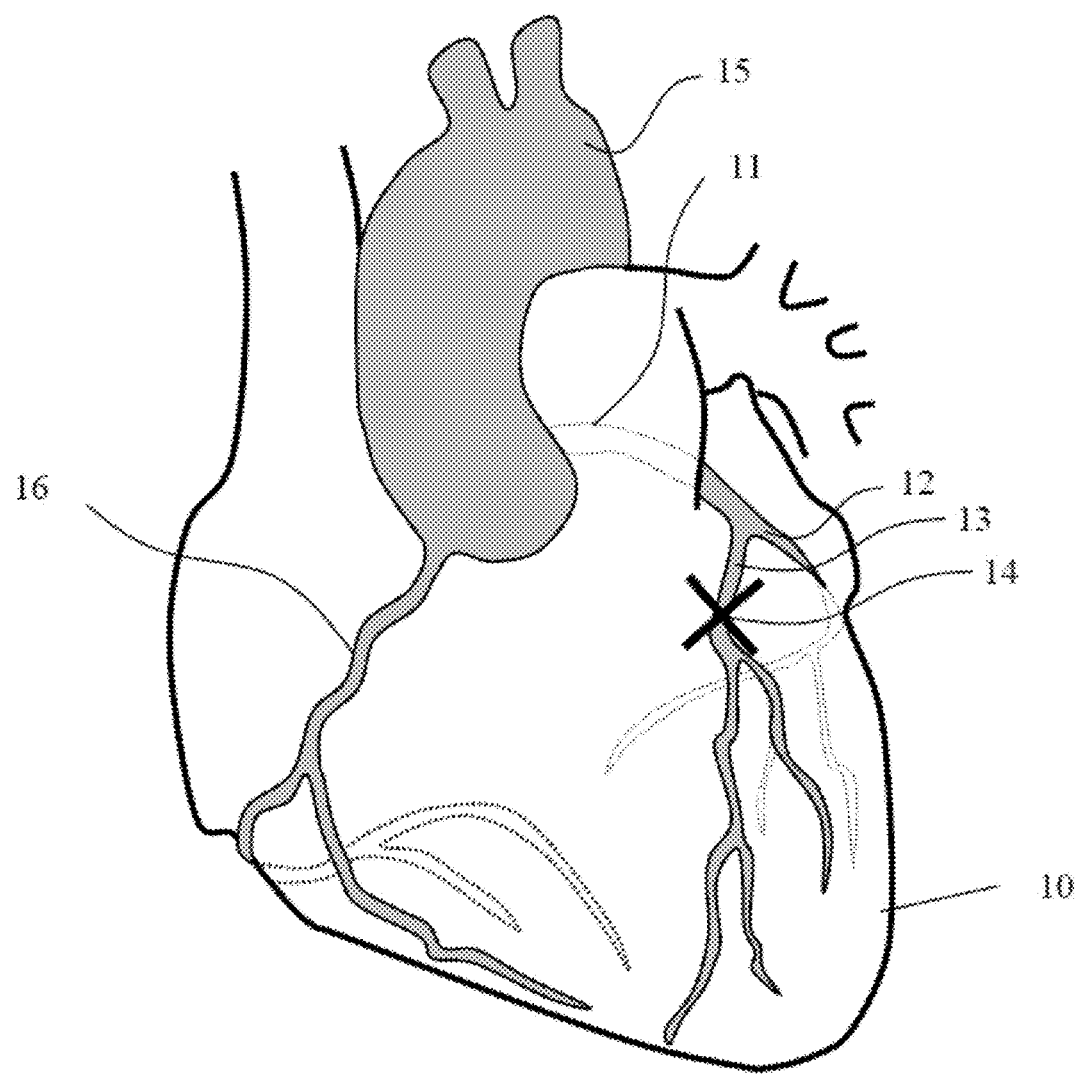
FIG. 1 schematically shows the target vessel in the heart when performing a coronary artery ligation to induce a myocardial infarction.

Described herein is a biodegradable elastomeric patch suitable for reducing or treating tissue deficiencies and damage resulting from a variety of cardiac and cardiovascular conditions, including, without limitation, deficiencies that are congenital or resulting from disease or injury. Generally, the biodegradable elastomeric patch can be used anywhere in the cardiac or cardiovascular system where there is a need to provide mechanical support to soft tissue, to encourage the growth of new tissue and/or to increase cell survival. The biodegradable elastomeric patch may optionally comprise therapeutic agents and/or cells.

The biodegradable elastomeric patch provides therapeutic or prophylactic benefits to animals, especially humans, in whom the cardiac or cardiovascular tissue is injured or diseased (i.e., by ischemic injury). The elastomeric patch may be used, for example and without limitation, in any condition in which cardiac or cardiovascular tissue is weakened and in which the strength provided by the patch can provide a therapeutic or prophylactic benefit. The patches are also suitable for delivery of drugs and other therapeutic agents to the heart or components of the cardiovascular system in situ.

Cardiac function may be compromised by a variety of congenital defects, diseases or injuries which may be treated with the biodegradable elastomeric patch. The mechanical support provided by the biodegradable elastomeric patch makes it useful for treating any condition in which the cardiac muscle or vasculature is weakened. Accordingly, the biodegradable elastomeric patch may be useful for treating cardiac or cardiovascular disease associated with, for example and without limitation, myocardial infarction, congestive heart failure (left or right sided), congenital heart disease, or cardiomyopathies, including idiopathic myopathy and endocarditis. The biodegradable elastomeric patch may be used to reinforce vasculature including arteries and veins and is also therefore useful for treating or preventing aneurysms. The biodegradable elastomeric patch may also be used to reinforce any portion of the heart, including a free wall, outflow tract, valve, or septum. In one non-limiting example, the biodegradable elastomeric patch may be used to reconstruct an individual's right ventricular outflow tract (RVOT) for treating a congenital defect. In another non-limiting example, the biodegradable elastomeric patch may be used for a defect or deficiency in a cardiac valve. In addition, undesirable ventricular cardiac remodeling that occurs after a sub-acute myocardial infarction, including left ventricular remodeling may also be reduced or prevented by implanting the patch on the heart of the effected individual.

Trauma to the heart, including for example, puncture or abrasive wounds may also be treated by applying an elastomeric patch.

The biodegradable elastomeric patch can also be used to promote tissue growth and to provide a supplemental source of cells, which can contribute to healing of the myocardium and causing differentiation of precursor cells to mature cells, such as myocardial cells. Thus, for example, the elastomeric patch may be used to promote growth of new myocardial cells following myocardial infarction in the infarcted region of the heart.

The biodegradable elastomeric patch described herein comprises a polymer-containing composition (polymer composition) comprising one or more polymers. The polymers are biodegradable, biocompatible, and elastomeric. Polymer(s) may be natural (occurring in nature) or synthetic. Natural polymer(s) can be obtained from biological sources, such as, without limitation, mammalian or vertebrate tissue, as in the case of certain extracellular matrix compositions. Natural polymers also can be manufactured synthetically and/or modified. Polymer(s) include, for example and without limitation, mono-polymer(s), copolymer(s), block polymer(s), block copolymer(s), cross-linked polymer(s), non-cross-linked polymer(s), linear-, branched-, comb-, star-, and/or dendrite-shaped polymer(s), where polymer(s) can be formed into, for example and without limitation, hydrogel, fiber, woven, mesh, or non-woven mesh, such as, for example and without limitation, as a mesh formed by electrospinning.

Generally, the polymer compositions suitable for the patches described herein may be any polymer that is biodegradable, biocompatible, and elastomeric. By "biodegradable", it is meant that the polymer, once implanted and placed in contact with bodily fluids and/or tissues, will degrade either partially or completely through chemical, biochemical and/or enzymatic processes. Non-limiting examples of such chemical reactions include acid/base reactions, hydrolysis reactions, and enzymatic cleavage. In certain embodiments, the polymer(s) comprise labile chemical moieties, non-limiting examples of which include esters, anhydrides, polyanhydrides, or amides, which can be useful in, for example and without limitation, controlling the degradation rate of the polymer composition and/or the release rate of therapeutic agents from the polymer composition. Alternatively, the polymer(s) may contain peptides or biomacromolecules as building blocks which are susceptible to chemical reactions once placed in situ. For one non-limiting embodiment, the polymer may comprise a polypeptide comprising alanine-alanine-lysine, which confers enzymatic lability to the polymer. In another non-limiting embodiment, the polymer composition may comprise a biomacromolecular component derived from an ECM. For example, the polymer may contain the biomacromolecule collagen so that collagenase, which is available in situ can degrade the collagen.

In some non-limiting embodiments, the polymer composition is selected so that it degrades in situ on a timescale that is similar to an expected rate of healing of the tissue damage or repair. Non-limiting examples of useful in situ degradation rates include between one week and one year, between two weeks and 10 months, and between one month and six months or increments therebetween. When the polymer is used to treat a patient after a myocardial infarction, it may be advantageous to tailor the polymer degradation rate to the size of the infarction as determined by methods such as echocardiography or magnetic resonance imaging. For example, when the size of the infarction is large, it would be advantageous to choose a more slowly degrading polymer, so that the entire infarction has a chance to heal before the polymer completely degrades.

The polymer compositions used to make the biodegradable elastomeric patch are preferably biocompatible. By "biocompatible," it is meant that a polymer composition or device and their normal degradation products in vivo are cytocompatible and are substantially non-toxic and non-carcinogenic in a patient within useful, practical and/or acceptable tolerances. By "cytocompatible," it is meant that the polymer composition or device can sustain a population of cells and/or the polymer composition or device, and degradation products thereof are not cytotoxic and/or carcinogenic within useful, practical and/or acceptable tolerances. For example, the polymer when placed in a human myocardial cell culture does not adversely affect the viability, growth, adhesion, and number of cells. In another non-limiting example, the polymer, when implanted in a patient does not cause a substantial adverse reaction or substantial harm to cells and tissues in the body, for instance, the polymer composition or device does not cause necrosis, inflammation, an immune response or an infection resulting in harm to tissues from the implanted patch. In one non-limiting embodiment, the polymer composition or device is "biocompatible" to the extent they are acceptable for use in a human or veterinary patient in accordance with applicable governmental regulatory provisions, such as, without limitation, those of the US Food and Drug Administration.

According to certain non-limiting embodiments, the polymer compositions useful in making the patch described herein are elastomeric. For example and without limitation, the elastomeric polymer has physical properties similar to that of soft tissue. For example and without limitation, in certain embodiments, the polymers used to make the biodegradable elastomeric patch are highly distensible. Examples of suitable polymers include those that have a breaking strain ranging from about 100% to about 900%, for example between 200% and 800%, or between 325% and 600%. In other non-limiting embodiments, the breaking strain of the polymer is between 50% and 100%. Further, it is often useful to select polymers with tensile strengths of from 10 kPa to 30 MPa, including increments therebetween, such as from 5 MPa to 25 MPa, and between 8 MPa and 20 MPa. In certain non-limiting embodiments, the initial modulus is between 10 kPa to 100 MPa and increments therebetween, such as 10 MPa and 90 MPa, and between 20 MPa and 70 MPa.

The polymer composition can be prepared by any method known in the art. According to one non-limiting embodiment, the polymer composition comprises a biodegradable polymeric portion, an isocyanate derivative, and a diamine chain extender. For example and without limitation, formation of the polymeric composition comprises at least two steps. In the first step, a prepolymer is formed. For example and without limitation, the prepolymer comprises an isocyanate-terminated polymer, which is formed by reacting a biodegradable polymer with an isocyanate derivative. In the second step, the prepolymer can be further reacted to form chemical bonds between prepolymer molecules. For example and without limitation, the isocyanate-terminated prepolymer is reacted with a diamine chain extender, which reacts with the isocyanate moiety to form chemical bonds between prepolymer molecules. Preparation of polymer compositions may include other steps, including, for example and without limitation, catalytic steps, purification steps, and separation steps.

The polymer compositions described herein comprise one or more of the many biodegradable polymers known in the art. The biodegradable polymers may comprise homopolymers, copolymers, and/or polymeric blends comprising, without limitation, one or more of the following monomers: glycolide, lactide, caprolactone, dioxanone, and trimethylene carbonate. In one non-limiting embodiment, the polymer composition comprises a polycaprolactone. In another embodiment, the polymer composition comprises a polycaprolactone diol. In yet another embodiment, the polymer composition comprises a triblock copolymer comprising polycaprolactone, poly(ethylene glycol), and polycaprolactone blocks. As used herein, an "isocyanate derivative" is any molecule or group that is terminated by the moiety —N=C=O. Isocyanate derivates also include, without limitation, monoisocyanates and polyisocyanates, such as diisocyanates and triisocyanates. In one non-limiting embodiment, the isocyanate derivative is 1,4-diisocyanatobutane. As used herein, a "chain extender" is any molecule or group that reacts with an isocyanate derivative to extend chains of polymers. In one non-limiting embodiment, the chain extender is a diamine that allows for extending the chain of the prepolymer. In one non-limiting embodiment, the diamine is putrescine (1,4-diaminobutane). In another non-limiting embodiment, the diamine is lysine ethyl ester. In yet another non-limiting embodiment, the diamine is a peptide fragment comprising two or more amino acids. For example and without limitation, the diamine can be the peptide fragment alanine-alanine-lysine, which can be cleaved enzymatically by elastase.

In one non-limiting embodiment, the polymer composition comprises a biodegradable poly(ester urethane) urea elastomer (PEUU). A non-limiting example of such a PEUU is an elastomeric polymer made from polycaprolactone diol (MW 2000) and 1,4-diisocyanatobutane, using a diamine chain extender such as putrescine. One non-limiting example or a method for preparing a PEUU polymer is a two-step polymerization process whereby polycaprolactone diol (MW 2000), 1,4-diisocyanatobutane, and diamine are combined in a 2:1:1 molar ratio. In the first step to form the prepolymer, a 15 wt % solution of 1,4-diisocyanatobutane in DMSO (dimethyl sulfoxide) is stirred continuously with a 25 wt % solution of polycaprolactone diol in DMSO. Then, stannous octoate is added and the mixture is allowed to react at 75° C. for 3 hours. In the second step, the prepolymer is reacted with a diamine to extend the chain and to form the polymer. In one embodiment, the diamine is putrescine, which is added drop-wise while stirring and allowed to react at room temperature for 18 hours. In one embodiment, the diamine is lysine ethyl ester, which is dissolved in DMSO with triethylamine, added to the prepolymer solution, and allowed to react at 75° C. for 18 hours. After the two step polymerization process, the polymer solution is precipitated in distilled water. Then, the wet polymer is immersed in isopropanol for three days to remove any unreacted monomers. Finally, the polymer is dried under vacuum at 50° C. for 24 hours.

In another non-limiting embodiment, the polymer composition comprises poly(ether ester urethane) urea elastomer (PEEUU). For example and without limitation, the PEEUU may be made by reacting polycaprolactone-b-polyethylene glycol-b-polycaprolactone triblock copolymers with 1,4-diisocyanatobutane and putrescine. In one non-limiting embodiment, PEEUU is obtained by a two-step reaction using a 2:1:1 reactant stoichiometry of 1,4-diisocyanatobutane:triblock copolymer:putrescine. According to one non-limiting embodiment, the triblock polymer can be prepared by reacting poly(ethylene glycol) and ε-caprolactone with stannous octoate at 120° C. for 24 hours under a nitrogen environment. The triblock copolymer is then washed with ethyl ether and hexane, then dried in a vacuum oven at 50° C. In the first step to form the prepolymer, a 15 wt % solution of 1,4-diisocyanatobutane in DMSO is stirred continuously with a 25 wt % solution of triblock copolymer in DMSO. Then, stannous octoate is added and the mixture is allowed to react at 75° C. for 3 hours. In the second step, putrescine is added drop-wise under stirring to the prepolymer solution and allowed to react at room temperature for 18 hours. The PEEUU polymer solution is then precipitated with distilled water. The wet polymer is immersed in isopropanol for 3 days to remove unreacted monomer and dried under vacuum at 50° C. for 24 hours.

In general, the biodegradable elastomeric patches described herein may be made using common processes known in the polymer and textile arts. The biodegradable elastomeric patch may take many different forms. In certain non-limiting embodiments, the biodegradable elastomeric patch comprises a thin, flexible fabric that can be sewn directly on a region to be treated. In another non-limiting embodiment, the patch comprises a non-woven mat that can be saturated in place at the site of implantation or affixed using a medically acceptable adhesive. In certain embodiments, the biodegradable elastomeric patch is as thick as the heart wall of a patient and used to treat conditions where the integrity of the heart wall is compromised, such as in atrial septal defects. In one embodiment, the patch is substantially planar having much greater dimension in two dimensions and a substantially smaller dimension in a third, comparable to bandages, gauze, and other substantially flexible, flat items. Besides flat, planar patches, biodegradable elastomeric patches can also have three-dimensional shapes useful for treating tissue deficiencies, such as plugs, rings, wires, cylinders, tubes, or disks. A useful range of thickness for the biodegradable patch is between 50 µm to 3.5 cm, between 100 µm to 3.0 cm, and between 300 µm and 2.5 cm, including increments therebetween.

In one embodiment, the biodegradable elastomeric patch is made by using solvent casting to form a film. This method involves dissolving the polymer in a suitable organic solvent and casting the solution in a mold. For example and without limitation, a 3 wt % solution of the polymer in N,N-dimethylformamide (DMF) is cast into a polytetrafluoroethylene coated dish. Then, DMF typically is evaporated at room temperature and the film is further dried under vacuum.

Although the biodegradable elastomeric patches may be porous or non-porous, it may be advantageous in certain cases to use a process that produces a porous elastomeric patch. Non-limiting examples of such processes include solvent casting/salt leaching, electrospinning, and thermally induced phase separation. As used herein, the term "porosity" of a material refers the portion of the material by volume comprising pores, with the remainder of the volume being the polymer portion of the material. For instance, a polymer composition with a porosity of 85% would have 85% of its volume containing pores (e.g., spaces, gaps, holes openings, as in the non-limiting example of a sponge, which may be filled with any material other than the polymer the remainder of the material comprises) and 15% of its volume containing the polymer. In certain embodiments, the porosity of the patch is at least 60%, 65%, 70%, 75%, 80%, 85%, or 90%.

In another non-limiting embodiment, the biodegradable elastomeric patch is made by using solvent casting and salt leaching. This method involves dissolving the polymer into a suitable organic solvent and then casting the solution into a mold containing small particles of predetermined size (known as porogens). Examples of suitable porogens include, without limitation, inorganic salts, crystals of saccharose, gelatin spheres or paraffin spheres. By adjusting the porogen size and/or the ratio of porogen to solvent, the porosity of the final elastomeric patch may be adjusted. After casting, the solvent is evaporated, and the resulting polymer composition is immersed into a second solvent that dissolves the porogen, but not the polymer, to produce a porous, sheet-like structure.

In other non-limiting embodiments, electrospinning is used to fabricate the elastomeric patch. The process of electrospinning involves placing a polymer-containing fluid (for example and without limitation, a polymer solution, a polymer suspension, or a polymer melt) in a reservoir equipped with a small orifice, such as a needle or pipette tip and a metering pump. One electrode of a high voltage source is also placed in electrical contact with the polymer-containing fluid or orifice, while the other electrode is placed in electrical contact with a target (typically a collector screen or rotating mandrel). During electrospinning, the polymer-containing fluid is charged by the application of high voltage to the solution or orifice (for example, about 3 to about 15 kV) and then forced through the small orifice by the metering pump, providing a steady flow. While the polymer-containing fluid at the orifice normally would have a hemispherical shape due to surface tension, the application of the high voltage causes the otherwise hemispherically shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, which typically is biased between −2 to −10 kV. Optionally, a focusing ring with an applied bias (for example, 1 to 10 kV) can be used to direct the trajectory of the charged jet of polymer-containing fluid. As the charged jet of fluid travels towards the biased target, it undergoes a complicated whipping and bending motion. If the fluid is a polymer solution or suspension, the solvent typically evaporates during mid-flight, leaving behind a polymer fiber on the biased target. If the fluid is a polymer melt, the molten polymer cools and solidifies in mid-flight and is collected as a polymer fiber on the biased target. As the polymer fibers accumulate on the biased target, a non-woven, porous mesh is formed on the biased target.

The properties of the electrospun elastomeric patches described herein can be tailored by varying the electrospinning conditions. For example, when the biased target is relatively close to the orifice, the resulting electrospun mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice. In certain embodiments, the biased target is moved back and forth in a regular, periodic fashion, such that fibers of the non-woven mesh are substantially parallel to each other. When this is the case, the resulting non-woven mesh may have a higher resistance to strain in the direction parallel to the fibers, compared to the direction perpendicular to the fibers. In other embodiments, the biased target is moved relative to the orifice in a two- or three-dimensional pattern to create a non-woven mesh comprising one or more patterned layers with similar or different strand orientation, thickness, etc. In other embodiments, the biased target is moved randomly relative to the orifice, so that the resistance to strain in the plane of the non-woven mesh is isotropic. The properties of the electrospun elastomeric patches may also be varied by changing the magnitude of the voltages applied to the electrospinning system. In one particularly preferred embodiment, the electrospinning apparatus includes an orifice biased to 12 kV, a target biased to −7 kV, and a focusing ring biased to 3 kV.

In another non-limiting embodiment, thermally induced phase separation (TIPS) is used to fabricate the biodegradable elastomeric patch. This method involves dispersing the polymeric components in a solvent (for example, DMSO) and then injected into a pre-formed mold. The pre-formed mold can have any useful shape, such as a sheet or net, for example. The pre-formed mold is cooled to low temperature (for example, −80° C.), which causes the polymer components to separate out of the solvent. The pre-formed mold is then transferred to ethanol to extract the DMSO. In one embodiment, PEUU (10% w/v) is initially dissolved in DMSO at 80° C., injected into a pre-formed mold, cooled over three hours to −80° C., kept in ethanol at 4° C. for seven days, and freeze dried for 48 hours.

After fabricating the biodegradable elastomeric patch, the planar or three-dimensional surface of the patch can be functionally modified to promote cellular adhesion and migration. In one non-limiting example, the surface is first treated to introduce a reactive group on the surface by any process known in the art. Second, the activated surface is reacted with an adhesion-promoting peptide or group. The reactive group on the surface can be, for example and without limitation, a hydroxyl group or an amine group. In one embodiment, radio-frequency glow discharge is used to produce plasma containing ammonia gas and amine groups are introduced to the surface by treatment with the plasma. In another embodiment, radio-frequency glow discharge is used to introduce hydroxyl groups to the surface by treatment with plasma.

The activated surface can be modified with an adhesion-promoting peptide to promote cellular ingrowth into the patch. For example and without limitation, adhesion peptides known in the art include the ubiquitous RGDS, which is a recognition site for fibronectin, vitronectin, fibrinogen, von Willebrand factor, and collagen; LDV, REDV, PHSRN, and KNEED, which are recognition sites for fibronectin; YIGSR and IKVAV, which are recognition sites for laminin; and DGEA, a recognition site for collagen.

In one specific non-limiting embodiment, the patch is functionalized to present the peptide RGDS on its surface. First, the surface is treated with radio-frequency glow discharge containing ammonia gas to introduce amine groups. Ammonia-containing gas is generated by connecting a flask containing ammonia hydroxide (30 wt % solution) to the glow discharge reactor and maintaining pressure at $3 \times 10^{-3}$ Torr. The surface is further treated with 1,4-diisocyanatobutane to provide a reactive isocyanate group. Second, RGDS is attached to the activated surface. The activated surface is immersed in a solution of 20 μg/mL RGDS in PBS for 10 hours and then rinsed with PBS.

In certain embodiments, the polymer compositions used to make the biodegradable elastomeric patch are not only biocompatible, but also release therapeutic agents when they degrade within the patient's body. For example, the individual building blocks of the polymers may be chosen such that the building blocks themselves provide a therapeutic benefit when released in situ through the degradation process. In one non-limiting embodiment, one of the polymer building blocks is putrescine, which has been implicated as a substance that causes cell growth and cell differentiation.

One or more of therapeutic agents can be introduced into the patch by any useful method. In one non-limiting example, the therapeutic agent is introduced into the backbone of the polymer. By adding the therapeutic agent to the elastomeric polymer itself, the rate of release of the therapeutic agent may be controlled by the rate of polymer degradation. In another non-limiting example, the therapeutic agent is introduced when the patch is being made. For instance, during the solvent casting or TIPS process, the therapeutic agent can be added to the solvent with the polymer in the pre-formed mold. During the electrospinning process, the therapeutic agent can be electrosprayed onto the polymer being spun. In yet another non-limiting example, the therapeutic agent is introduced into the patch after the patch is made. For instance, the patch may be "loaded" with therapeutic agent(s) by using static methods. For instance, the patch can be immersed into a solution containing the therapeutic agent permitting the agent to absorb into and/or adsorb onto the patch. The patch may also be loaded by using dynamic methods. For instance, a solution containing the therapeutic agent can be perfused into the patch. In another instance, a therapeutic agent can be added to the biodegradable elastomeric patch before it is implanted in the patient.

Therapeutic agents within the patch can be used in any number of ways. In one non-limiting embodiment, a therapeutic agent is released from the patch. For example and without limitation, anti-inflammatory drugs are released from the patch to decrease an immune response. In another non-limiting embodiment, a therapeutic agent is intended to substantially remain within the patch. For example and without limitation, chemoattractants are maintained within the patch to promote cellular migration and/or cellular infiltration into the patch.

Generally, the therapeutic agents include any substance that can be coated on, embedded into, absorbed into, adsorbed to, or otherwise attached to or incorporated onto or into the biodegradable elastomeric patch that would provide a therapeutic benefit to a patient. For example, a biodegradable elastomeric patch comprising neurotrophic agents or cells that express neurotrophic agents may be placed near an infarcted region to promote neuronal growth and to ameliorate arrhythmogenesis which may result from the infarction. In another example, a patch comprising growth factors or cells that express growth factors may be placed on, adjacent to, or near damaged tissue to promote cell growth and vascularization. In one non-limiting embodiment, the therapeutic agent is mixed with a carrier polymer (i.e., polylactic-glycolic acid microparticles) which is subsequently incorporated within or otherwise processed with an elastomeric polymer to produce the patch.

In certain non-limiting embodiments, the therapeutic agent is a growth factor, such as a neurotrophic or angiogenic factor, which optionally may be prepared using recombinant techniques. Non-limiting examples of neurotrophic factors include nerve growth factor, brain-derived neurotrophic factor, neurotrophin-3, neurotrophin-4, neurotrophin-5, and ciliary neurotrophic factor. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors (IGF), platelet derived growth factor (PDGF), transforming growth factor-beta (TGF-β), pleiotrophin protein (neurite growth-promoting factor 1), and midkine protein (neurite growth-promoting factor 2). In one preferred embodiment, the growth factor is IGF-1. Commercial preparations of various growth factors, including neurotrophic and angiogenic factors, are available from R & D Systems, Minneapolis, Minn.; Biovision, Inc, Mountain View, Calif.; and ProSpec-Tany TechnoGene Ltd., Rehovot, Israel.

In certain embodiments, the therapeutic agent is an anti-inflammatory agent, such as, without limitation, a NSAID, such as salicylic acid, indomethacin, sodium indomethacin trihydrate, salicylamide, naproxen, colchicine, fenoprofen, sulindac, diflunisal, diclofenac, indoprofen sodium salicylamide; an anti-inflammatory cytokine; an anti-inflammatory protein; a steroidal anti-inflammatory agent; or an anti-clotting agents, such as heparin. Other drugs that may promote cardiac function may also be included.

In certain non-limiting embodiments, the therapeutic agent includes cells that are added to the biodegradable elastomeric patch before implantation. In such embodiments, it is often advantageous to use a porous biodegradable elastomeric patch, so that the cells may be incorporated into the porous structure, matrix, or scaffolding of the patch (a condition referred to as "microintegration"). In this way, most of the cells will have a tendency to be trapped within the porous structure of the patch. In certain embodiments, the microintegrated cells may remain after the biodegradable elastomeric patch has fully disintegrated within the patient. However, the microintegrated cells may also be merely cells that act as precursors to the final tissue that is formed when the biodegradable elastomeric patch has fully degraded.

In certain non-limiting embodiments, the therapeutic agent is released by genetically modified cells. Cells can be modified by any useful method in the art. For example and without limitation, the therapeutic agent is a growth factor that is released by cells transfected with cDNA encoding for the growth factor. Therapeutics agents that can be released from cells include, without limitation, a neurotrophic factor, such as nerve growth factor, brain-derived neurotrophic factor, neutrotrophin-3, neurotrophin-4, neurotrophin-5, and ciliary neurotrophic factor; a growth factor, such as basic fibroblast growth factor (bFGF), acidic fibroblast growth factor (aFGF), vascular endothelial growth factor (VEGF), hepatocyte growth factor (HGF), insulin-like growth factors (IGF), platelet derived growth factor (PDGF), transforming growth factor-beta (TGF-β), pleiotrophin protein (neurite growth-promoting factor 1), and midkine protein (neurite growth-promoting factor 2); an anti-inflammatory cytokine; and an anti-inflammatory protein. Non-limiting examples of cells that produce therapeutic agents include: any kind of stem cells, embryonic immature cells, smooth muscle cells, skeletal muscle derived cells, and endothelial cells. Various commercially available cell lines include Clonetics® Primary Cell Systems (Lonza Group, Inc., Switzerland) and ATCC.

In other non-limiting embodiments, the therapeutic agent is a cell from any useful cell line known in the art. For example and without limitation, the therapeutic agent comprises stem cells that are capable of cellular growth, remodeling, and/or differentiation. By way of example only, the cells that may be incorporated onto or into the biodegradable patch include stem cells, precursor cells, smooth muscle cells, skeletal myoblasts, myocardial cells, endothelial cells, and genetically modified cells. Various commercially available cell lines include Clonetics® Primary Cell Systems (Lonza Group, Inc., Switzerland) and ATCC.

Cells may be microintegrated with the biodegradable elastomeric patch using a variety of methods. For example and without limitation, the elastomeric patch may be submersed in an appropriate growth medium for the cells of interest, and then exposed to the cells. The cells are allowed to proliferate on the surface and interstices of the elastomeric patch. The elastomeric patch is then removed from the growth medium, washed if necessary, and implanted in a patient. Alternatively, the cells may be placed in a suitable buffer or liquid growth medium and drawn onto and/or into the patch by using vacuum filtration. In another particularly useful embodiment, the cells of interest are dissolved into an appropriate solution (e.g., a growth medium or buffer) and then sprayed onto a biodegradable elastomeric patch while the patch is being formed by electrospinning. In one particular embodiment, the cells are placed in a solution that is biased and then electrosprayed onto the biodegradable elastomeric patch while it is being electrospun. By way of example only, the cells that may be incorporated onto or into the biodegradable patch include stem cells, precursor cells, smooth muscle cells, skeletal myoblasts, myocardial cells, endothelial cells, and genetically modified cells. In one embodiment, the genetically modified cells are capable of expressing a therapeutic substance, such as a growth factor. Non-limiting examples of cells that produce therapeutic agents are described above, include a neurotrophic factor, such as nerve growth factor, brain-derived neurotrophic factor, neurotrophin-3, neurotrophin-4, neurotrophin-5, and ciliary neurotrophic factor; a growth factor, such as basic fibroblast growth factor (bFGF), acidic fibroblast growth factor (aFGF), vascular endothelial growth factor (VEGF), hepatocyte growth factor (HGF), insulin-like growth factors (IGF), platelet derived growth factor (PDGF), transforming growth factor-beta (TGF-β), pleiotrophin protein (neurite growth-promoting factor 1), and midkine protein (neurite growth-promoting factor 2); an anti-inflammatory cytokine; and an anti-inflammatory protein.

As used herein, the terms "implanted" and "implantation" refer to an act of delivering a patch to a site within the patient and of affixing the patch to the site. The patient may be human or animal. The patch may be delivered by any surgical procedure, including minimally invasive techniques, such as laparoscopic surgery, as well as invasive techniques such as thoracic surgery or open heart surgery. The site of the implant can be, for example and without limitation, inside the heart, on the outer surface of the heart, or may connect the inner and outer surfaces of the heart. The site can be either on or near the tissue that is damaged or deficient. In a non-limiting example, when the biodegradable patch is used to treat a patient after sub-acute myocardial infarction, the biodegradable elastomeric patch is implanted over the infarcted region. The patch may be any useful shape including regular geometric shapes (e.g., circle, square, etc.) or irregular shapes. Often, it is useful to determine the required size of the patch prior to the surgery, by using an imaging technique, non-limiting examples of which include echocardiography and magnetic resonance imaging. Furthermore, the biodegradable elastomeric patch may be designed to possess anisotropic mechanical properties and then specifically oriented in a particular direction with respect to the surrounding tissue (e.g., heart muscle) prior to implantation.

The biodegradable elastomeric patch may be affixed to the site by any method known in the art. The patch may be implanted by using any surgical fasteners, non-limiting examples of which include sutures, staples, or adhesives, such as fibrin-based adhesives, for example. In one non-limiting embodiment, the patch is attached to the left ventricular surface of the heart following myocardial infarction by using sutures. When applying the biodegradable elastomeric patch to the surface of the heart, it is often advantageous to gently scrape the surface of the heart to be covered (e.g., an infarcted region) prior to implantation in order to cause slight bleeding and the formation of a blood clot. It is also advantageous to suture the biodegradable elastomeric patch while the patch is under a slight amount of tension.

EXAMPLES

Example 1

Implantation of a Biodegradable Elastomeric Patch on the Left Ventricle Following Coronary Artery Ligation to Induce an Infarction This example shows that the implantation of an elastomeric, biodegradable PEUU patch onto the heart following sub-acute myocardial infarction preserved left ventricular geometry and contractile function and promoted contractile phenotype smooth muscle tissue formation in chronic stage.

Adult female Lewis rats (Harlan Sprague Dawley, Indianapolis, Ind.) weighing (200-250 g), were used in this study. The research protocol followed the National Institutes of Health guidelines for animal care and was approved by the University of Pittsburgh's Institutional Animal Care and Use Committee and Children's Hospital of Pittsburgh Animal Research Care Committee. Animals were anesthetized by inhalation of 3.0% isoflurane and were intubated and connected to a rodent volume controlled mechanical ventilator (model 683, Harvard Apparatus, Holliston, Mass.). Mechanical ventilation was performed at a respiratory rate of 60-70 cycles/min and a tidal volume of 1.0-2.0 mL under 1.5 to 2.5 isoflurane anesthesia with 100% oxygen (2 L/min). Electrocardiogram and blood pressure were continuously monitored. The heart was exposed through a left thoracotomy. FIG. 1 schematically depicts the heart 10 and the target vessel 13 for inducing an infraction. In one embodiment of inducing an infarction, the target vessel 13 is the descending coronary artery and a suture is placed in the ligation site 14 to promote necrosis of the anterior wall of the left ventrical. The left coronary artery 11, circumflex artery 12, aorta 15, and right coronary artery 16 are shown for reference. In this example, the proximal left anterior descending coronary artery (LAD) was circumferentially ligated with a 7-0 polypropylene suture. Myocardial ischemia was confirmed by regional cyanosis and ST segment elevation by electrocardiography. The incision was closed in layers with 4-0 silk continuous sutures.

Two weeks after the coronary artery ligation, animals were anesthetized and examined using echocardiography for infarct size as estimated by the percentage of scar area (akinetic or dyskinetic regions) to left ventricular free wall (LVFW) area. A total of 26 rats with infarcts greater than 25% of the LVFW were randomly divided into 2 groups. In the first group, each animal (patch group n=14) was implanted with a circular patch made of polyester urethane urea (PEUU) (6 mm diameter×300 µm thickness, 85% porosity). PEUU was synthesized from butyl diisocyanate, poly(caprolactone) (2000 MW), and putrescine and processed. Briefly, a thermally induced phase separation technique was used for processing wherein 10 wt % PEUU in DMSO was quenched at −80° C. Prior to implantation, the PEUU patches were sterilized by immersion in 100% ethanol for 30 minutes, followed by immersion in PBS and exposure to the ultraviolet light source in a laminar flow hood for 1 hour. Through a left thoracotomy, infarcted anterior wall was exposed. Before patch implantation, the epicardium of infarcted cardiac muscle was scraped with a surgical knife (6 mm circle size). Using 7-0 polypropylene with over-and-over sutures, the anterior infracted myocardium was covered with PEUU patch. In the second group, each animal received a sham repair (infarction control group; n=12) in which the infarcted anterior wall was exposed via a left thoracotomy, but no patch was implanted. Additionally, six age-matched rats without coronary ligation underwent a sham operation for normal control.

Echocardiography was performed at the patch implantation (0 week), 4 weeks, and 8 weeks after PEUU patch implantation. Rats were anesthetized with continuous inhalation of 1.5% isoflurane with 100% oxygen (2 L/min) using a nose cone. Standard transthoracic echocardiography was performed using the Acuson Sequoia C256 system with a 13-MHz linear ultrasonic transducer (15L8; Acuson Corporation, Mountain View, Calif.) in a phased array format. B-mode measurements on the left ventricular short axis view (papillary muscle level) were performed. The end-diastolic (EDA) and end-systolic (ESA) left ventricular internal cavity area were measured by tracing of endocardial border. The left ventricular fraction of area change (% FAC) was estimated as, % FAC=[(EDA−ESA)/EDA]×100.

The harvested heart was frozen in 2-methylbutane, which was pre-cooled in liquid nitrogen. The embedded frozen left ventricular tissues were serially sections into left ventricular transverse direction at 8 μm thickness. The standard hematoxylin and eosin (H&E) staining and immunohistochemical staining were performed in each sample. Sections for immunohistochemistry were fixed with 2% paraformaldehyde for 5 minutes and reacted with an antibody against alpha-smooth muscle actin (α-SMA, Sigma, St Louis, Mo.), caldesmon, calponin, smooth muscle myosin heavy chain 2 (SMMHC-2), and SM-22α (Abcam, Cambridge, Mass.). Nuclei were stained with 4',6-Diamidino-2-phenyindole (DAPI, Sigma).

The harvested hearts were analyzed using optical microscopy and transmission electron microscopy (TEM). Specifically, optical microscopy was used to determine left ventricular wall thickness of the PEUU implanted left ventricular myocardium. In each left ventricular sample, five different microscopic fields (100×, TE200, Nikon, Tokyo, Japan) for the wall thickness measurement. The wall thickness of the infracted anterior wall (patch implanted area) was analyzed using the NIH image program and Adobe Photoshop (Adobe, San Jose, Calif.). In the TEM studies, two hearts from each group were cannulated through the aorta and perfusion-fixed with 2.5% glutaraldehyde in 0.1 mol/L phosphate buffer (pH 7.4) for 30 minutes, followed by immersion in the same fixative overnight at 4° C. They were cut into 1-mm cubes and postfixed in 1% buffered osmium tetroxide, dehydrated through graded ethanol, and embedded in epoxy resin. Thin sections (80 nm), double-stained with uranyl acetate and lead citrate, were examined with JEOL 1210 TEM system (JEOL USA, Peabody, Mass.).

Additionally, a passive left ventricular inflation test was performed. At eight weeks after PEUU implantation, the rat was anesthetized with 5% isoflurane with 100% oxygen and a median sternotomy was performed. The heart was exposed and arrested by apical injection of 2 mL of a hypothermic and hyperkalemic buffered arresting solution (68 mM NaCl, 60 mM KCl, 36 mM $NaHCO_3$, 2.0 mM $MgCl_2$, 1.4 mM $Na_2SO_4$, 11 mM dextrose, 30 mM butanedione monoxime, 10,000 U/l of heparin). The heart was excised, rinsed, and the coronary circulation flushed by retrograde perfusion through an aortic cannula with 5 mL of arresting solution. After perfusion, coronary arteries were occluded at the proximal site and mitral leaflets were completely closed by suture with 7-0 polypropylene. For LV surface strain measurement, 4 graphite particle (~0.5 mm diameter) markers at 6 mm apart were placed in a square configuration on the center of infarcted LV epicardial surface using an ultrapure low-viscosity, fast cure, butyl-cyanoacrylate ester glue (Vetabond, 3M, St. Paul, Minn.). The heart was then submerged in a chamber containing arresting solution that allows entrance of a boroscope, which is coupled to a CCD camera for imaging. As the region of interest (6 mm diameter) was sufficiently small, it was deemed acceptable to use a single camera for strain tracking and dual-camera, stereo imaging of the curved surface was not necessary. Markers were identified and tracked continuously via a custom LabVIEW program. Pressure was applied to the LV via a volume-infusion pump (model sp210w, World Precision Instruments) which formed a continuous connection with the lured cannula and a 2-Fr micromanometer-tipped catheter (model SPR631, Millar Instruments; Houston, Tex.). Therefore, during infusion, real-time strains in both directions (circumferential, $E_{11}$ and longitudinal, $E_{22}$) and the applied pressure were digitally recorded simultaneously. Pressure-strain (P-E) relations were determined for each group (normal, infarct, and patch; n=4 for each) by infusing arresting solution to a maximum pressure of 30 mmHg with no detectable leakage from the aortic or mitral valve.

Figure 2A:
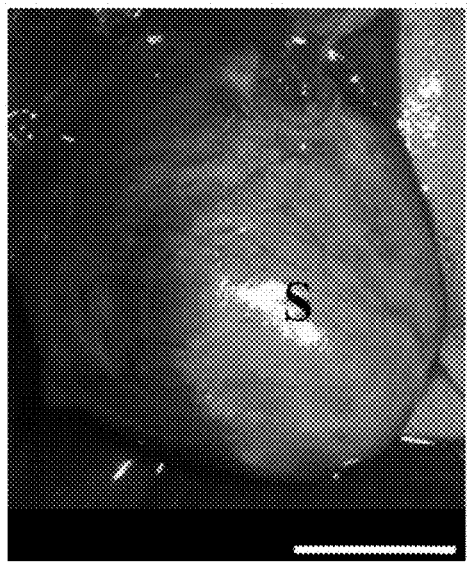
FIGS. 2A-2D are representative photographs of the left ventricle portion of the heart at eight weeks after an implant in the infarcted region of the left ventricle. The PEUU patched group received a PEUU patch two weeks after an induced myocardial infraction, where the control group did not receive any implant after an induced infarction.
Figure 2B:
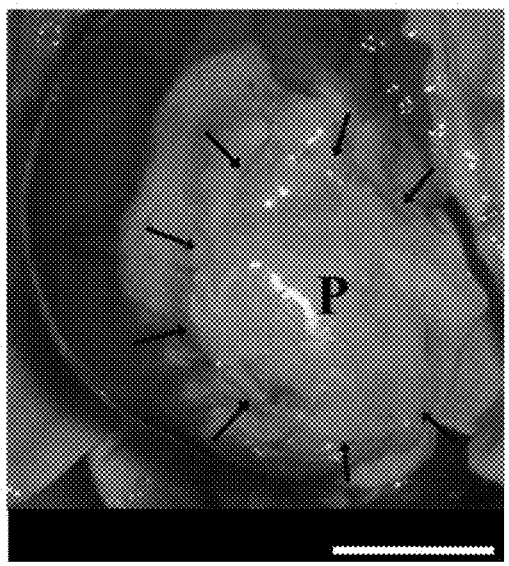
Figure 2C:
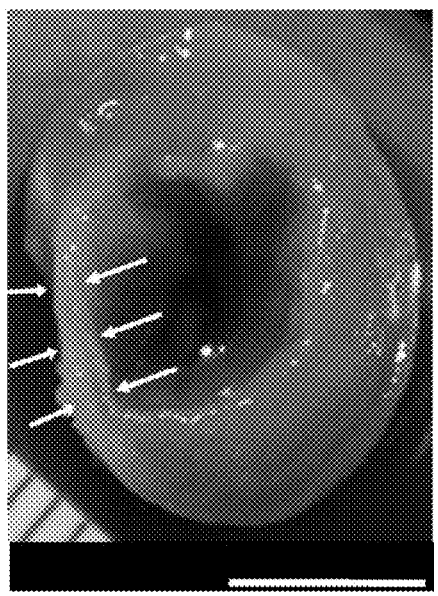
Figure 2D:
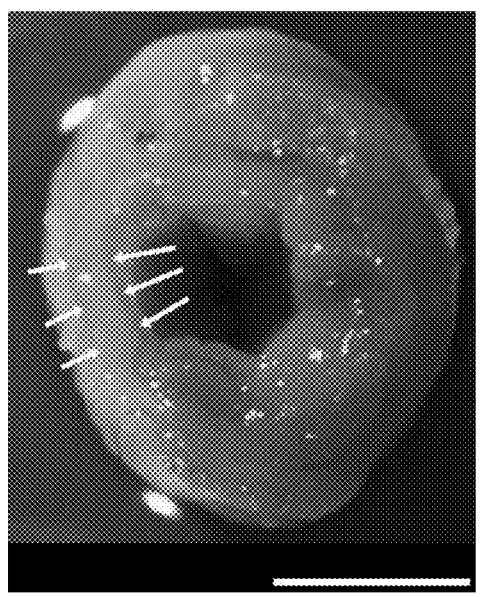

There was no early or late postoperative death or serious infection following PEUU patch implantation. At 8 weeks, the PEUU material had no strong adhesion with chest wall, and was covered with connective tissue on the surface. FIG. 2A shows that the PEUU was well merged and restored the ventricular size and shape in comparison with the infarction control group, which is shown in FIG. 2A. FIG. 2C shows the cross-section of the infarction control group and FIG. 2D shows the cross-section of the implanted wall with PEUU patches.

Figure 3A:
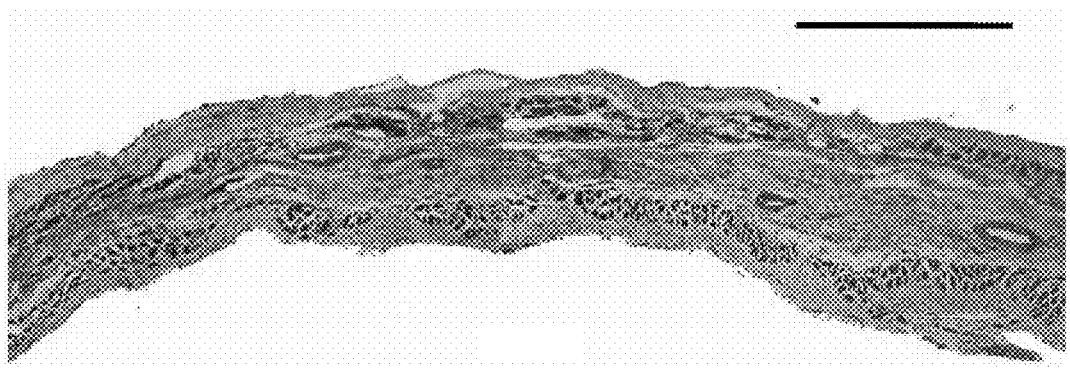
FIGS. 3A-3F are representative photomicrographs of hematoxylin and eosin (H&E)-stained and immunohistochemically-stained myocardial wall at eight weeks after an implant in the infarcted region of the left ventricle.
Figure 3B:
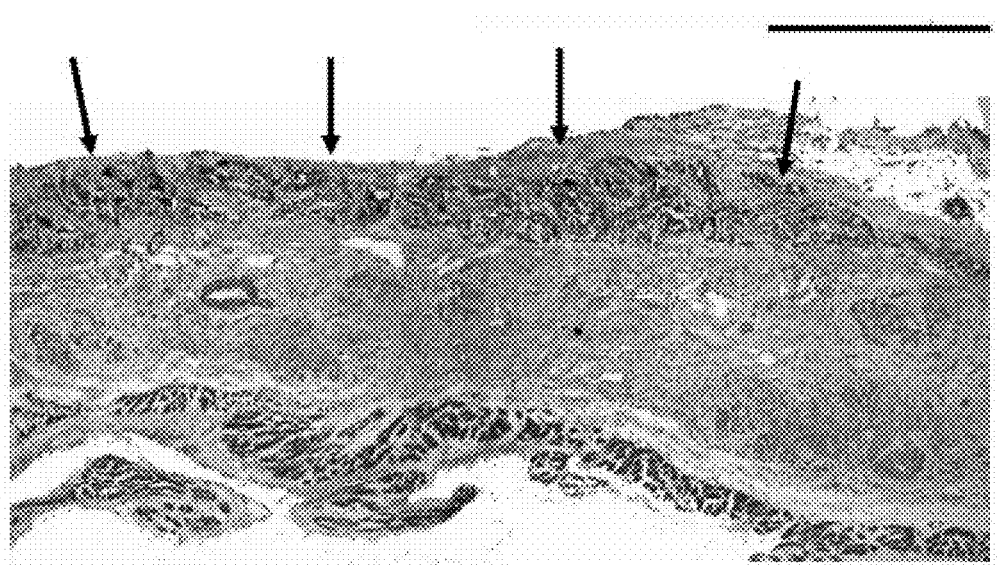
Figure 3C:
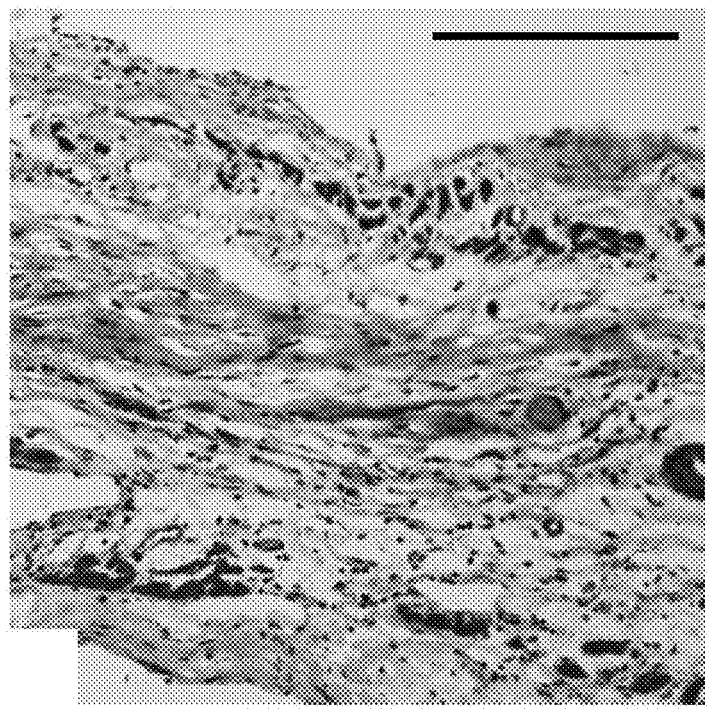
Figure 3D:
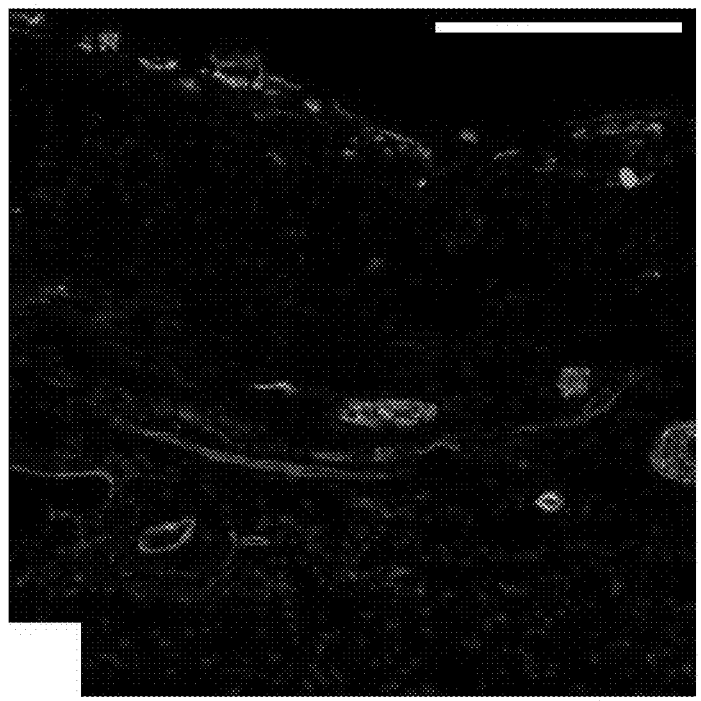
Figure 3E:
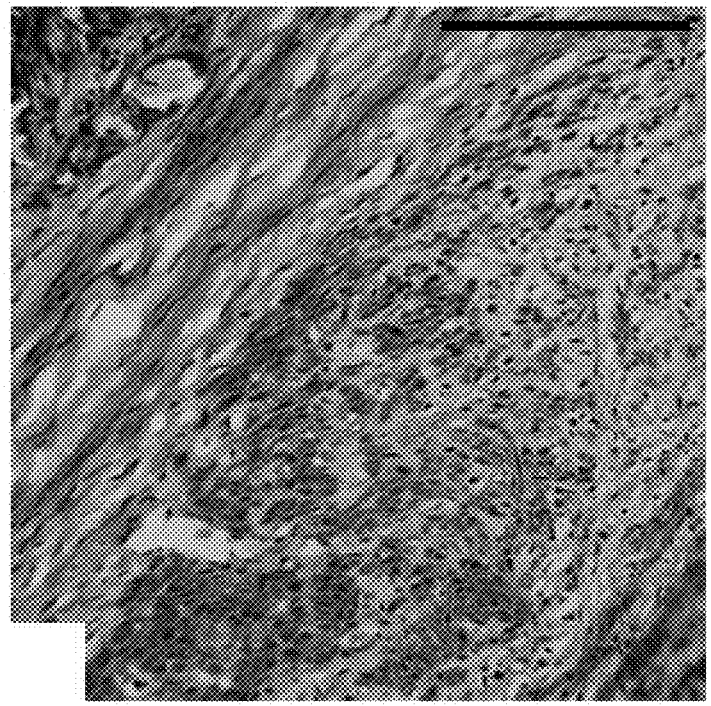
Figure 3F:
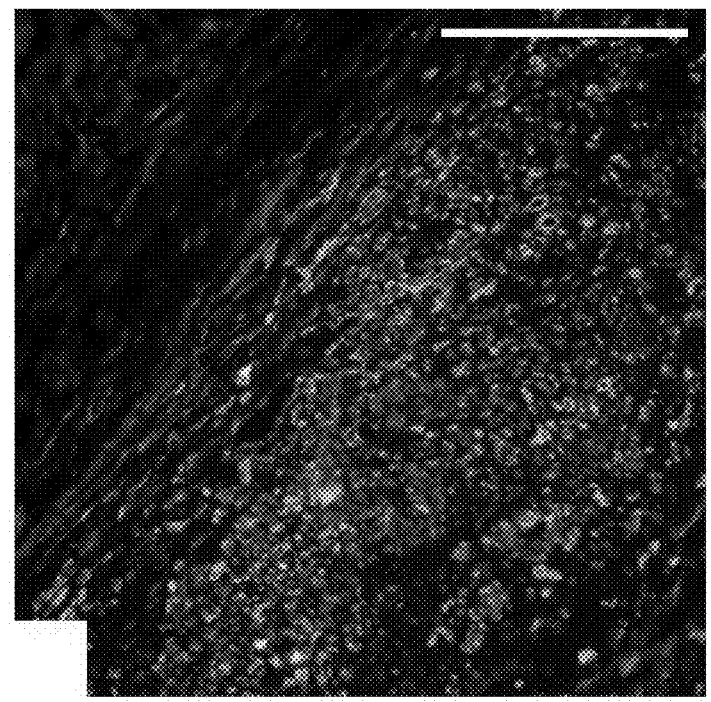
Figure 4A:
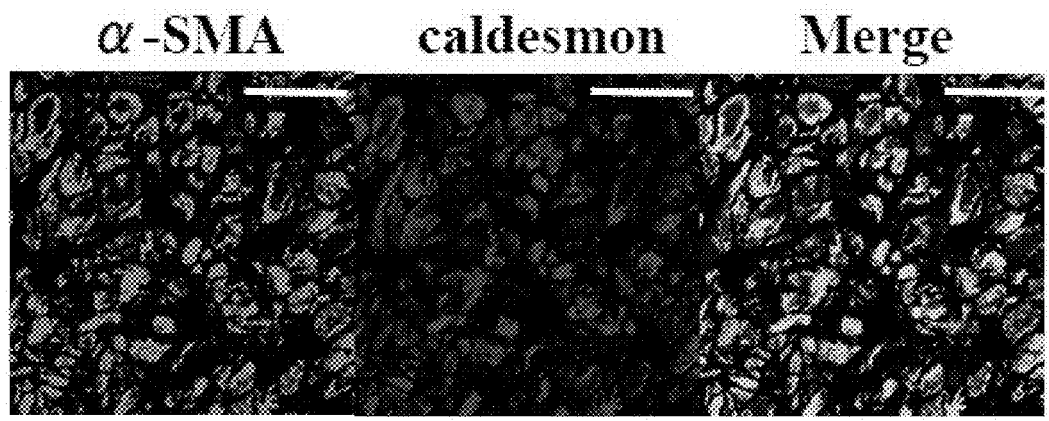
FIGS. 4A-D are photomicrographs of immunohistochemically-stained tissue from myocardial wall for the PEUU patched group.
Figure 4B:
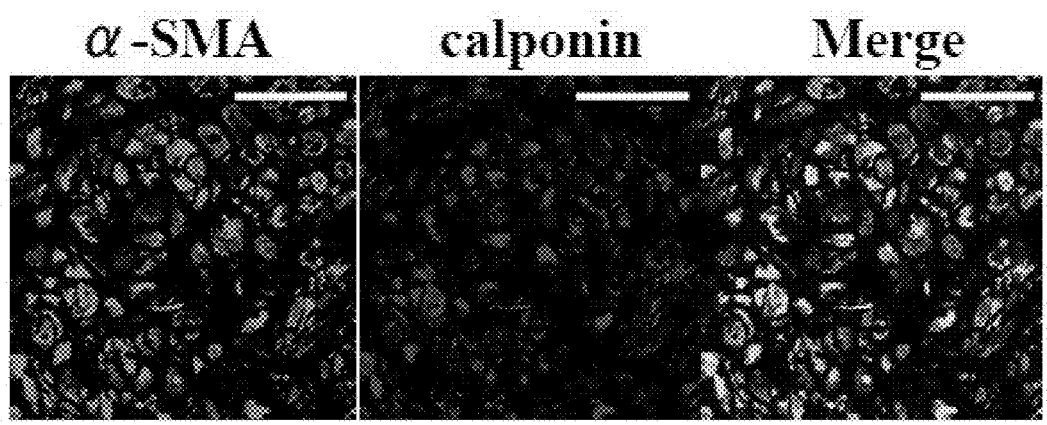
Figure 4C:
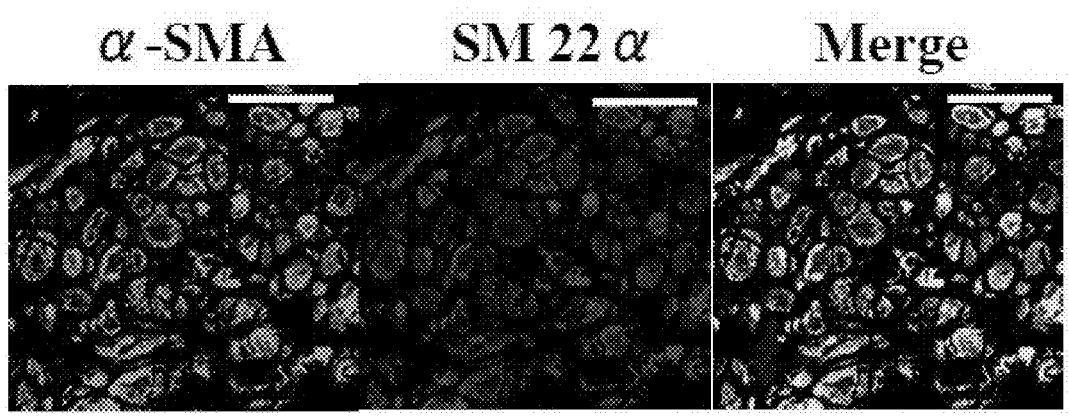
Figure 4D:
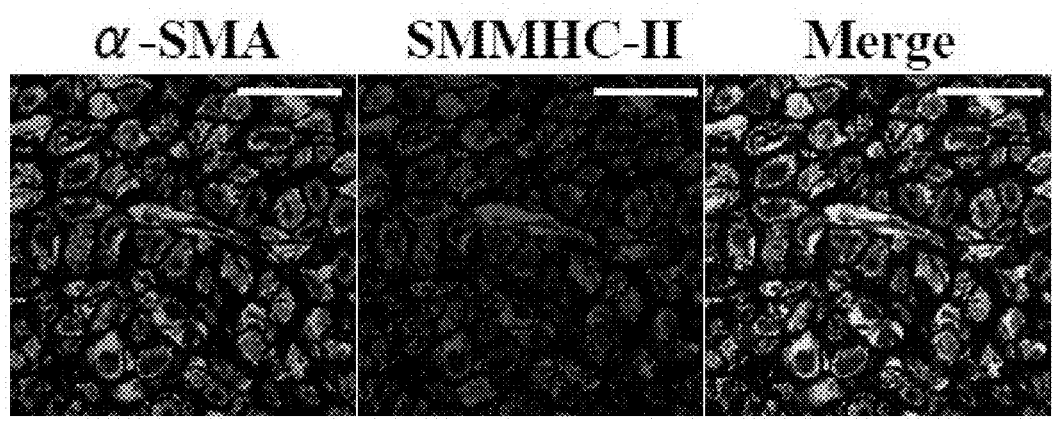
Figure 5A:
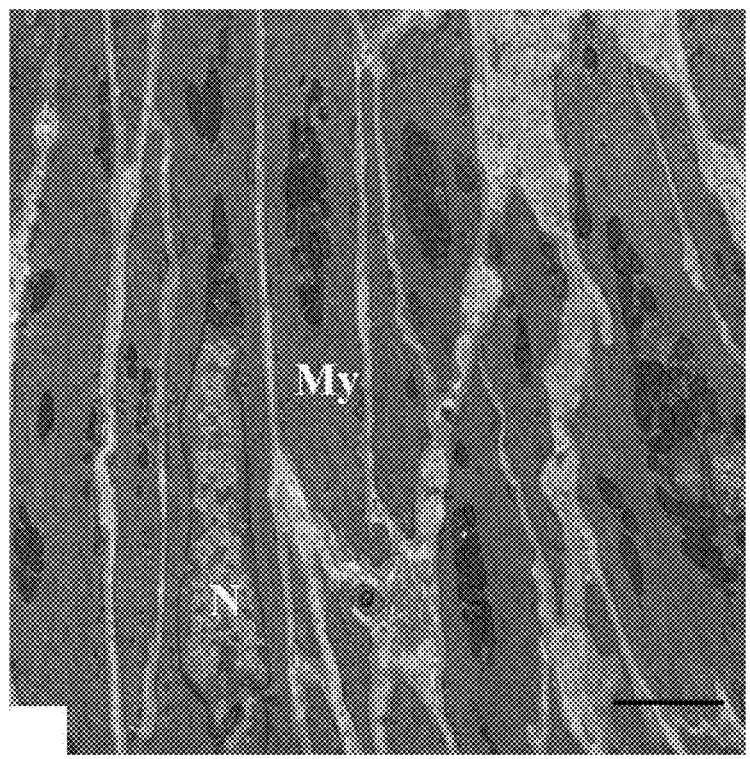
FIGS. 5A-5C are electron photomicrographs of smooth muscle cells from the myocardial wall for the PEUU patched group.
Figure 5B:
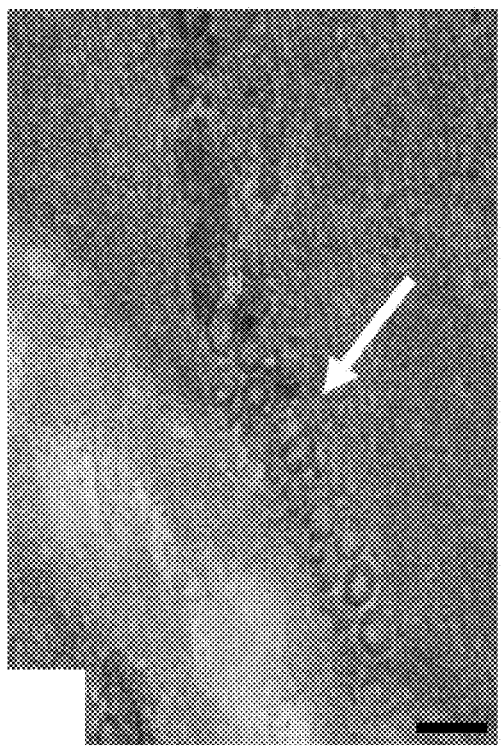
Figure 5C:
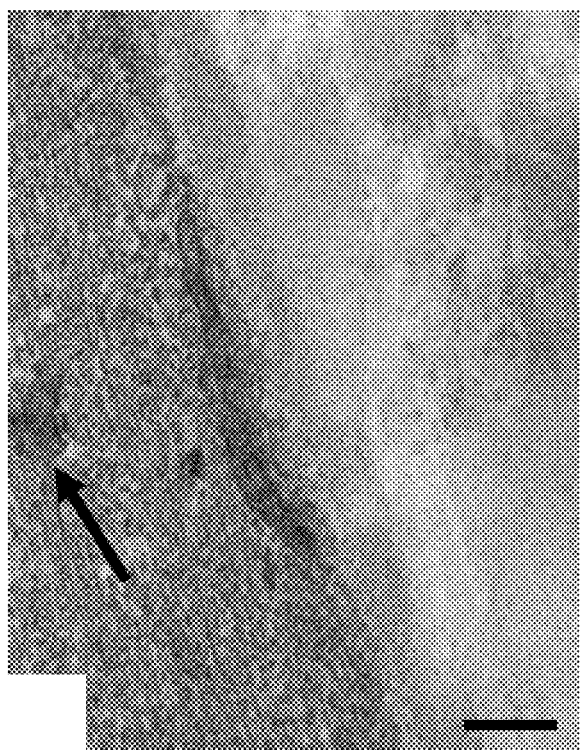
Figure 6:
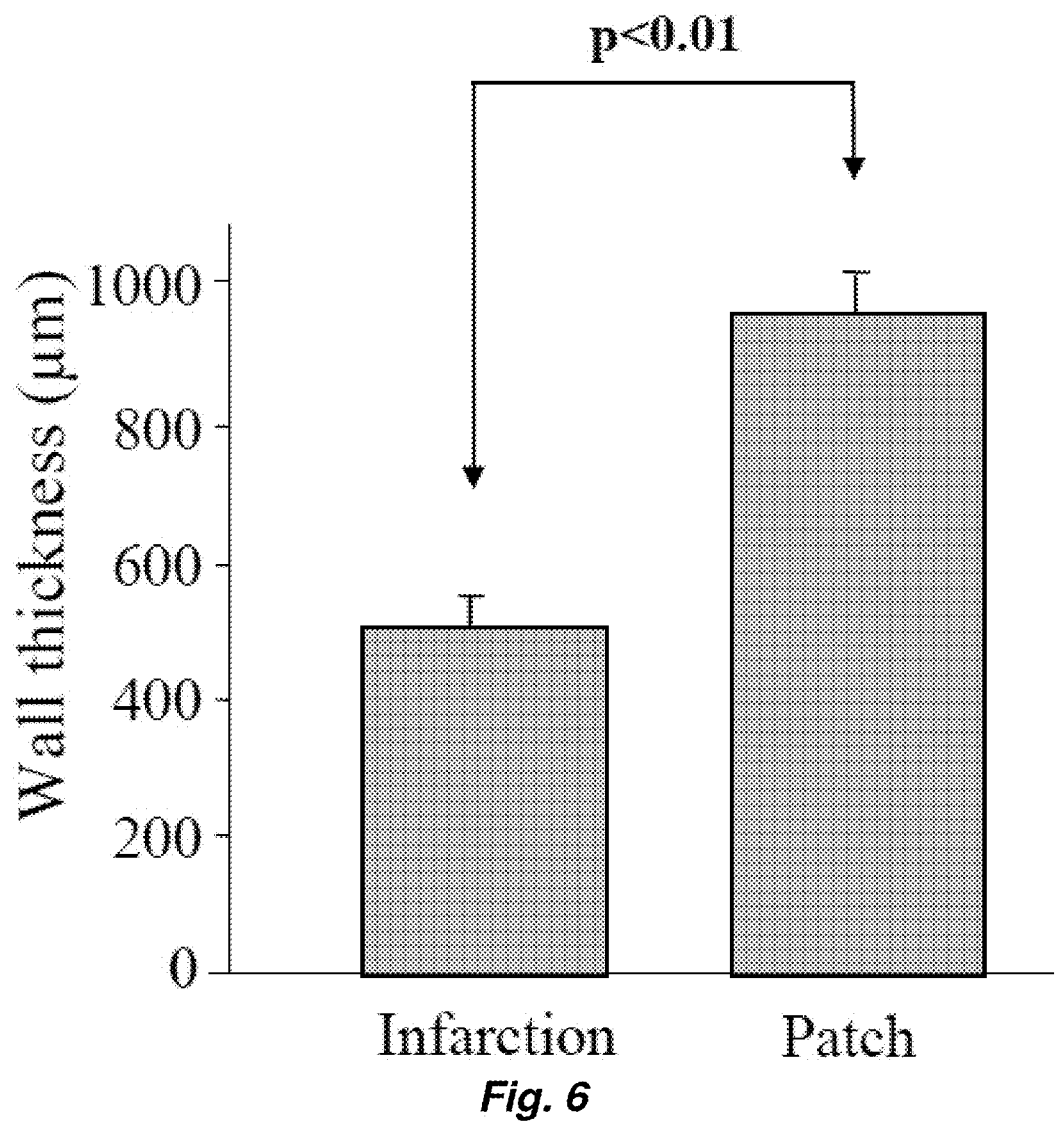
FIG. 6 is a graph comparing the left ventricular myocardial wall thickness of the PEUU patched group ("Patch") and the control group ("Infarction").

The majority of the PEUU patch was absorbed and the macrophages and fibroblasts infiltrated in the implantation area. FIG. 3 shows cross-sections of the left ventricular wall. FIGS. 3B, 3E, and 3F show a cross-section of an implanted wall with a PEUU patch. FIGS. 3A, 3C, and 3D show a cross-section of a wall for the infarction control. Implanted walls with PEUU patches were generally thicker and contained more dense and muscle-like bundles than the infarction control. FIGS. 4A-4D show that caldesmon, calponin, SM 22α, and SMMHC type II were co-expressed with α-SMA positive cells, which indicate mature contractile smooth muscle cells rather than myofibroblasts. FIG. 5A shows muscle-like bundles, which indicate that the aligned cells contained rich myofibril and had elongated cell morphology. These cells were found in extravascular areas and thus were not vascular smooth muscle cells. FIG. 5B shows some of the numerous caveoles along the membrane and FIG. 5C shows some of the dense bodies in cytoplasm that were observed. These ultrastructural features revealed that they had typical structure of mature contractile phonotype smooth muscle cells. FIG. 6 shows that the left ventricular myocardial wall of the PEUU implantation group was thicker than the infarction control group [PEUU; 985±89 (μm, SD) vs. Infarction control 482±62 P<0.05].

Figure 7A:
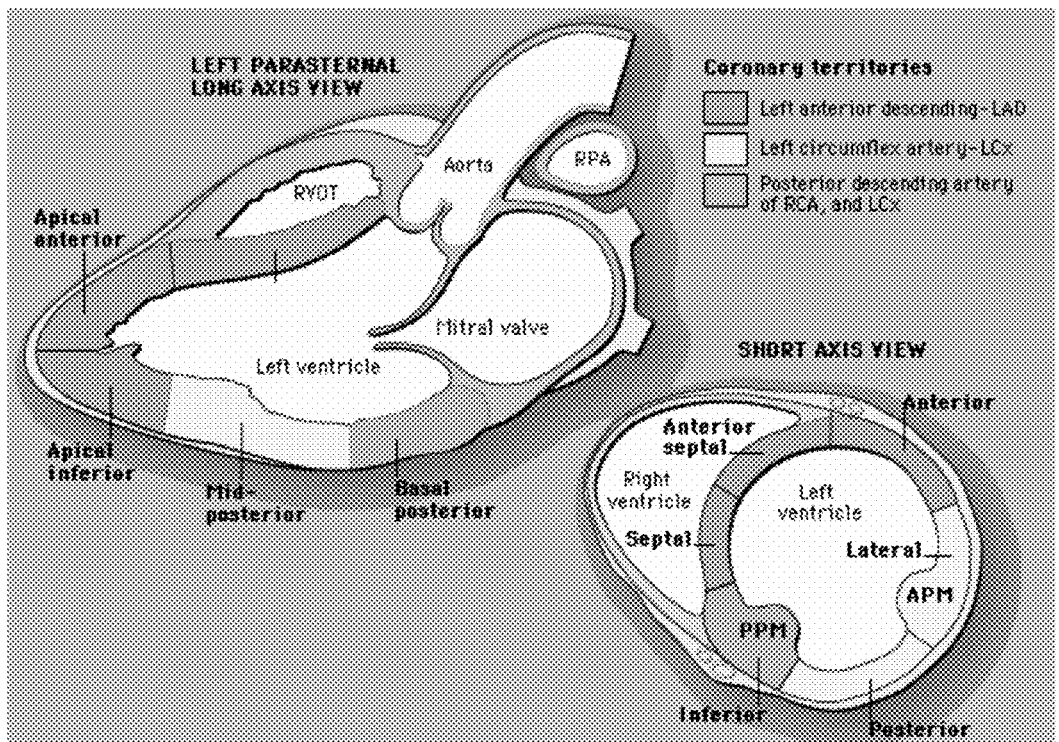
FIGS. 7A-7C show a non-limiting example of using echocardiography to assess the wall motion and the wall thickness of the anterior wall infarction.
Figure 7B:
Figure 7C:
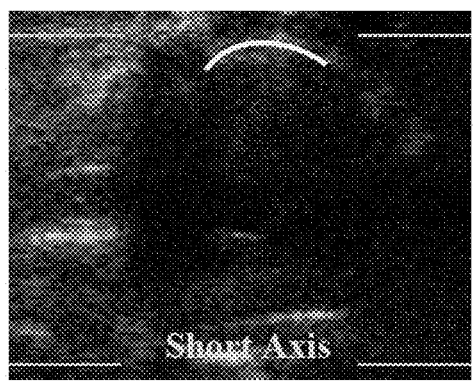
Figure 8A:
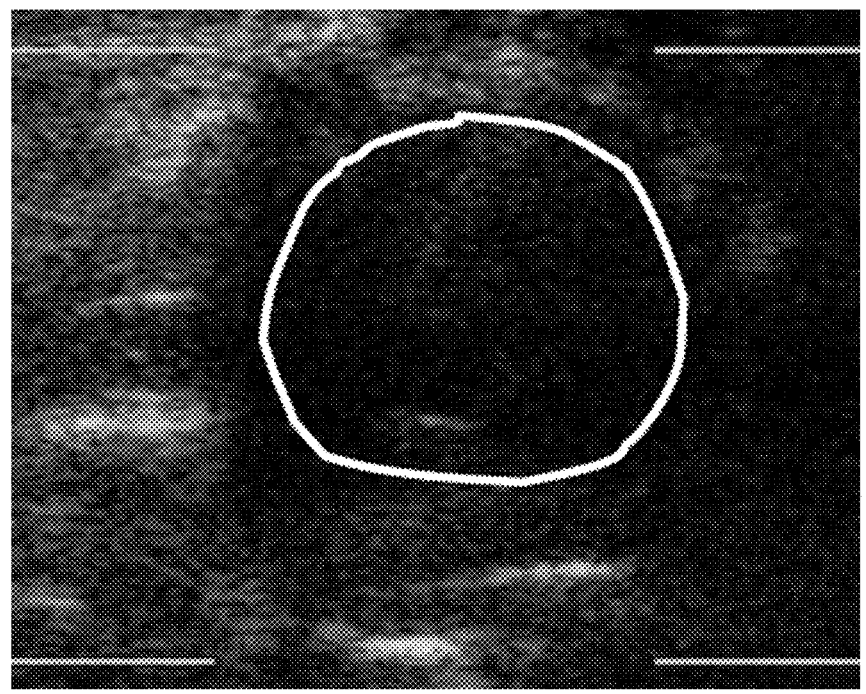
FIGS. 8A-B show a non-limiting example of using echocardiography to determine the end-diastolic left ventricle cavity area (EDA) for the PEUU patched group and the control group.
Figure 8B:
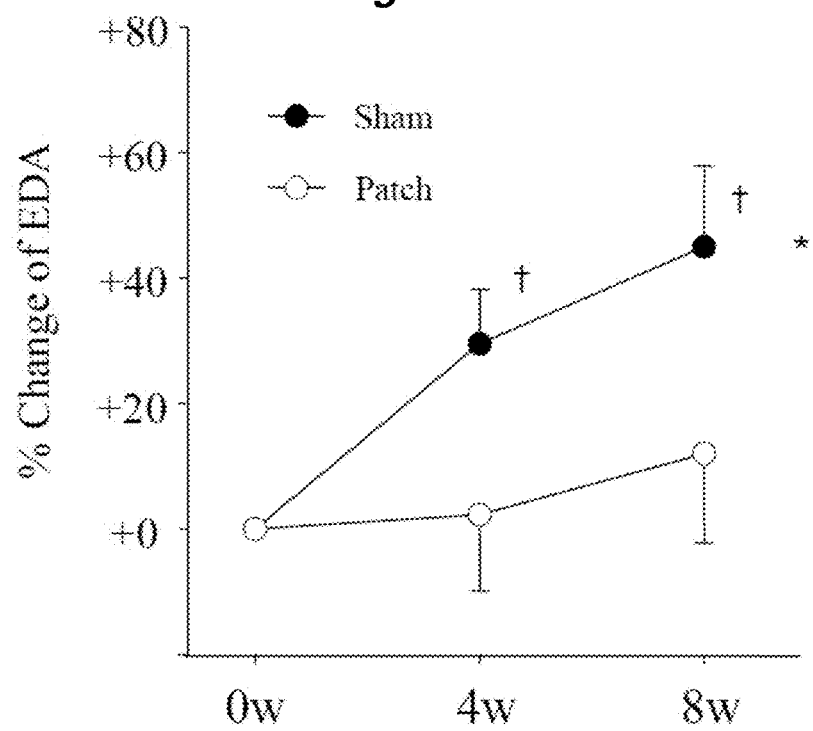

Echocardiography was also used to assess the PEUU patched group and the infarction control group, which will be briefly discussed. FIG. 7A schematically shows the long axis and short axis views of the heart. FIG. 7B shows an echocardiograph of the long axis and FIG. 7C shows an echocardiograph of the short axis. The end-diastolic (EDA) and end-systolic (ESA) left ventricular internal cavity area were measured by tracing the endocardial border in the echocardiograph. FIG. 8A shows an example of measuring the EDA, where FIG. 8B shows an example of data obtained from those EDA measurements.

Figure 9A:
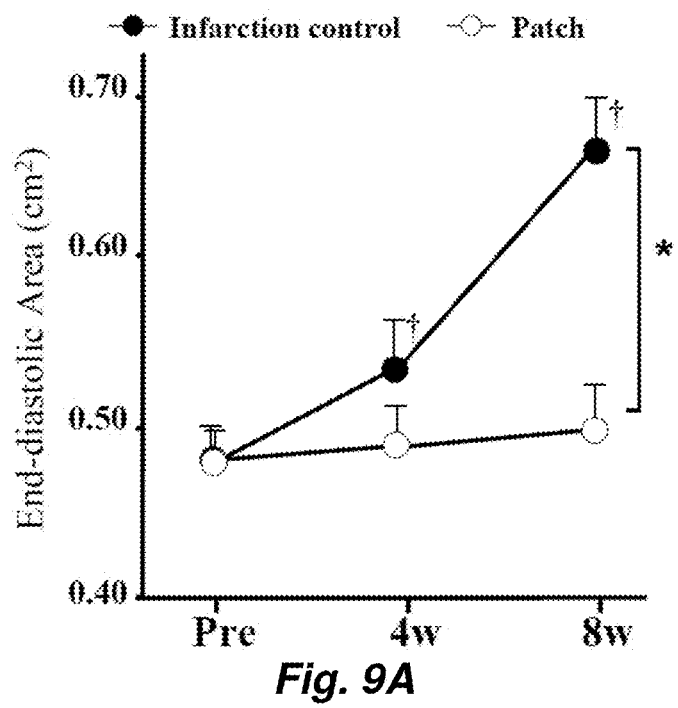
FIGS. 9A-9B are graphs of the end-diastolic left ventricle cavity area at eight weeks after implantation.
Figure 9B:
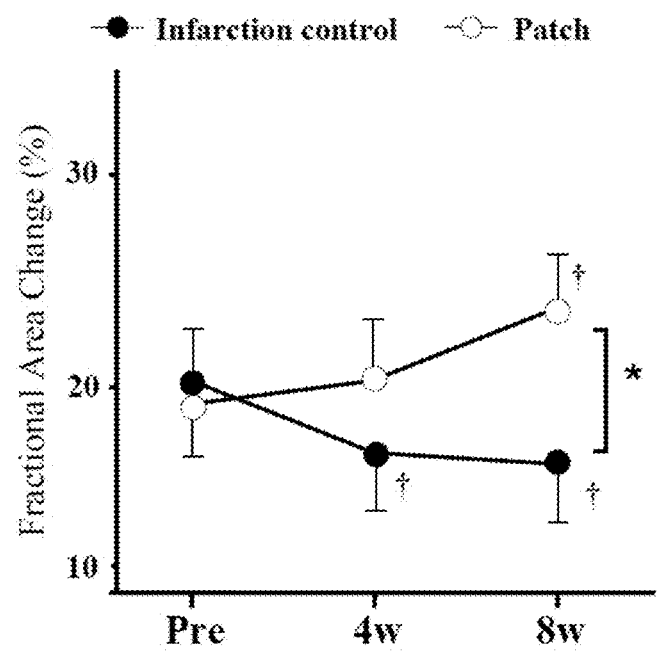

FIG. 9A shows the end diastolic left ventricular internal cavity area at time points of pre-implantation (Pre), four weeks (4 w), and eight weeks (8 w). At the time of the PEUU patch implantation (Pre), left ventricular end-diastolic left ventricular internal cavity area was significantly larger, and the fraction of area change was smaller than age matched normal controls indicating post infraction left ventricular dilatation and dysfunction (P<0.05). The PEUU patch group did not exhibit a change in the end-diastolic left ventricular internal cavity area following the patch implantation while at 8 weeks, the end-diastolic left ventricular internal cavity area of the infarction control was increased (P<0.05, vs 0 week), and significantly larger than the one of the PEUU patch group (P<0.05). FIG. 9B shows that the fraction of area change was increased in PEUU group by 8 weeks while the fraction of area change was decreased in the infarction control.

Figure 10A:
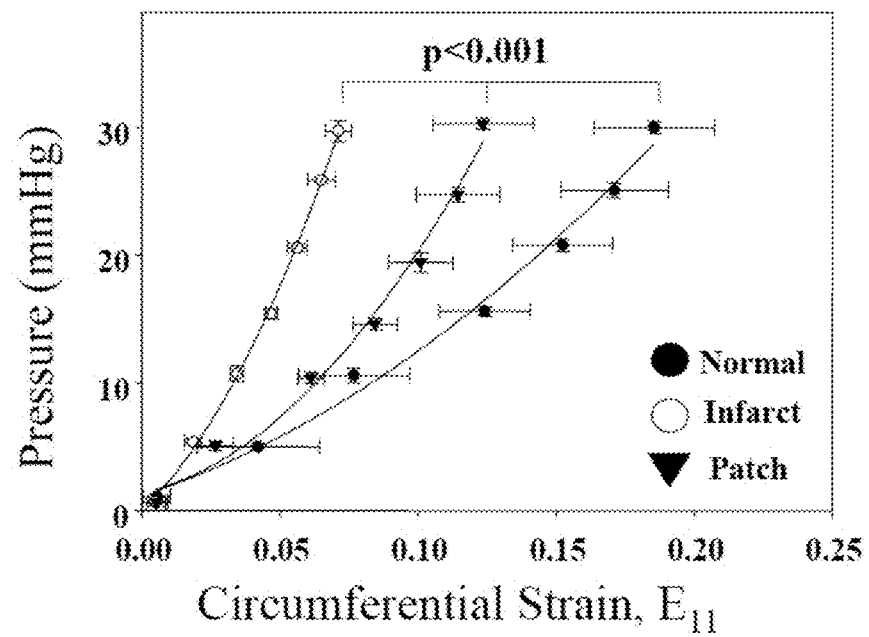
FIGS. 10A-10B are graphs of left ventricular myocardial strains for different pressures.
Figure 10B:
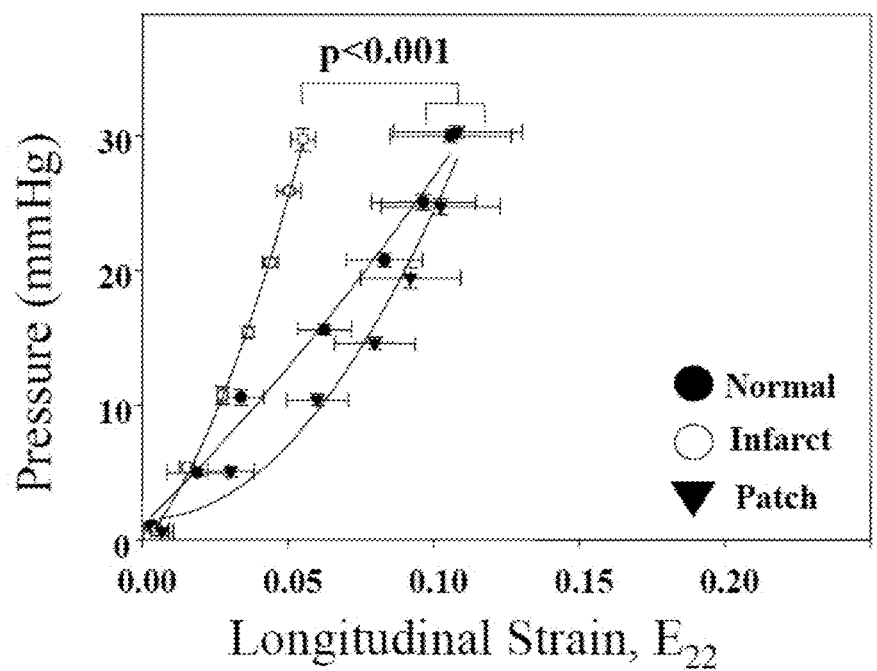

FIG. 10A shows the circumferential strain and FIG. 10B shows the longitudinal strain at different pressures for the PEUU patched group and the infarction control group. Both the circumferential and longitudinal left ventricular myocardial strains at given pressure of infarction control group exhibited the least compliance (P<0.01). On the other hand, the compliance of PEUU patch group fell down normal and infarction control wall, indicating normalized regional left ventricular myocardial compliance. There was a significant difference between all groups (P<0.01).

The thickness of the area covered with PEUU patch, even excluding the material area, is significantly thicker than infarction control and the compliance of the patched site fell between normal cardiac muscle and infarcted fibrous wall, regardless of the wall thickness. Without wishing to be limited by theory, it is believed that the relative stiffness of the healing infarct influences mechanical forces, thereby affecting ventricular remodeling and performance. Also the thickened infarct wall, consisting of the bundles of the contractile phenotype cells with the increased myofibril and functional proteins for contraction, may improve the infarct wall motion by decreasing wall stress.

In this study, massive smooth muscle cell bundles beneath the PEUU material was observed by electron microscopy. This remodeling induced by PEUU coverage appears different from the typical cardiac remodeling after infarction. Without wishing to be limited by theory, it is believed that the smooth muscle cells may result from inhibition of granulation tissue cell apoptosis and that these smooth muscle cells with the contractile phenotype might have been transdifferentiated from the myofibroblasts in the infarct area. PEUU is biodegradable and almost all of the PEUU material was phagocytosed by macrophages after 8 weeks implantation. It is also speculated that strong mechanical support by PEUU patch inhibited apoptosis at the time of implant and the change of mechanical tension during its biodegradation stimulated proliferation and differentiation of contractile smooth muscle cell bundles in the infarcted tissue beneath the material.

In the study presented in this example, all data are expressed as the mean±the standard deviation. By means of the SPSS software package for Windows version 9.0 (SPSS Inc, Chicago Ill.), the wall thickness in each group was compared by 1-way analysis of variance. The number of vessels was compared by Student t-test. The echocardiography data and the pressure-strain analysis were compared by 2 way repeated ANOVA with Tukey test.

Example 2

Implantation of a Biodegradable Elastomeric Patch on the Right Ventrical Following a Surgical Defect in the Right Ventricular Outflow Tract In this example, an elastomeric, biodegradable polyester urethane urea (PEUU) was processed into circular scaffolds and used to replace a surgical defect in the right ventricular outflow tract (RVOT) of adult rats. The PEUU patch demonstrated suitable mechanical properties and biocompatible characteristics in the RVOT replacement model, permitting cellular integration and endocardial endothelialization with minimal inflammation.

Adult male syngeneic Lewis rats (Harlan Sprague Dawley, Inc) weighing 300-350 g were used for the RVOT replacement procedure. The research protocol followed the NIH guidelines for animal care and was approved by Institutional Animal Care and Use Committee of the University of Pittsburgh.

Figure 11A:
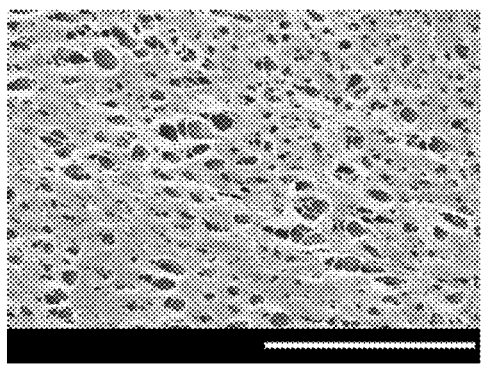
FIGS. 11A-11C are electron photomicrographs of the PEUU scaffold and patch.
Figure 11B:
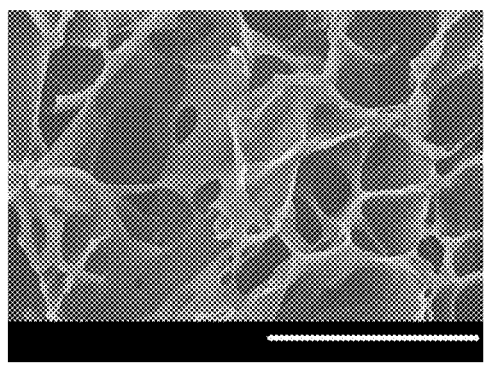
Figure 11C:
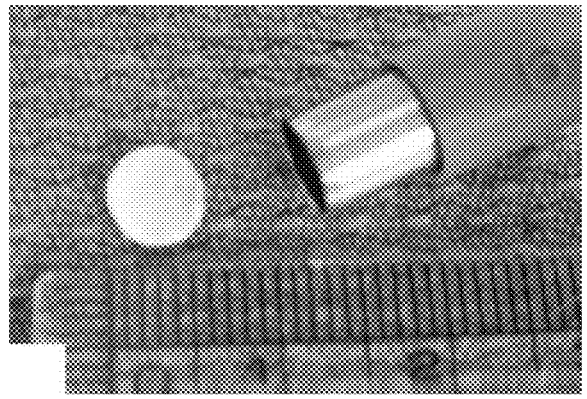

PEUU was synthesized from butyl diisocyanate, poly (caprolactone) (2000 MW), and putrescine and processed according to the methods of previous reports. Briefly, a thermally induced phase separation technique was used for processing wherein 10 wt % PEUU in DMSO was quenched at −80° C. This resulted in a scaffold with 85% overall porosity, interconnected pores, and a relatively smaller pore size on the surface skin. FIG. 11A shows the surface and FIG. 11B shows the cross-section of a PEUU scaffold. The PEUU scaffold was created in a mold that provided a material thickness of 0.4 mm. For control purposes ePTFE (IMPRA, Inc) also with a thickness of 0.4 mm was used. Both materials were cut into 6 mm diameter circular patches using a biopsy punch. FIG. 11C shows the PEUU scaffold as a 6 mm diameter patch. Patches were sterilized by immersion in 70% ethanol for 6 hours, followed by immersion in phosphate buffer saline solution (PBS), and exposure to an ultraviolet light source in a laminar flow hood for three hours.

After rinsing thoroughly with PBS, patches were implanted in the rat RVOT as described below. Rats were anesthetized by intramuscular injection of ketamine hydrochloride (22 mg/kg) and then intraperitoneal injection of sodium pentobarbital (30 mg/kg). Intubation was performed with ventilation at 60 cycles/min and a tidal volume of 2.0 mL under room air. The heart was exposed through a median sternotomy and a purse-string suture was placed in the RVOT free wall with 7-0 polypropylene to form a perimeter greater than 6 mm diameter (Ethicon). Both suture ends were then passed through a 24-gauge plastic vascular cannula (Becton Dickinson), which was used as a tourniquet. Upon tourniquet tightening, the RVOT wall inside the purse-string stitching was distended and resected. At that point the tourniquet was released slightly to demonstrate pulsatile bleeding, assuring transmural defect creation. A PEUU or ePTFE (n=12, each group) patch was sutured along the margin of the purse-string suture with an over-and-over method with 7-0 polypropylene to cover the defect. The tourniquet was then released and the purse-string suture removed. The chest incision was closed in layers with running sutures of 4-0 Vicryl (Ethicon). The first 3 days after surgery, buprenorphine (1 mg/kg) and cefuroxime (100 mg/kg) were administered intramuscularly twice a day.

At each scheduled explant time point (4, 8, and 12 weeks), animals from both groups were euthanized (n=4 per group) with intraperitoneal injection of an overdose of pentobarbital (100 mg/kg) following intramuscular injection of 500 units heparin. The heart was exposed through a repeated median sternotomy. After macroscopic photography of the heart in situ, it was harvested and frozen in 2-methylbutane, which was pre-cooled in liquid nitrogen.

The frozen heart tissue was serially cryosectioned into 10 μm thick specimens and processed for hematoxylin and eosin (H&E) or immunohistochemical evaluation. To assess the extracellular matrix, specimens were stained with the Masson Modified IMEB Trichrome Stain Kit (IMEB, Inc). Specimens for immunohistochemistry were reacted with an antibody against factor VIII (polyclonal 1:300; DAKO) to identify endothelial cells. Nuclei were stained with 4',6-Diamidino-2-phenyindole, DAPI (1:10,000; Sigma).

The tissue response (presence of macrophages, neovascularization, and cellular integration, respectively) was rated by three persons according to a relative scoring system: 0=no observation to +++=severe. The sections also were also examined for the formation of a fibrous capsule around the patches and cellular infiltration into the material.

Figure 12A:
FIGS. 12A-12B: are representative photographs of the right ventricle portion of the heart at twelve weeks after an implant in the free wall of the right ventricle.
Figure 12B:
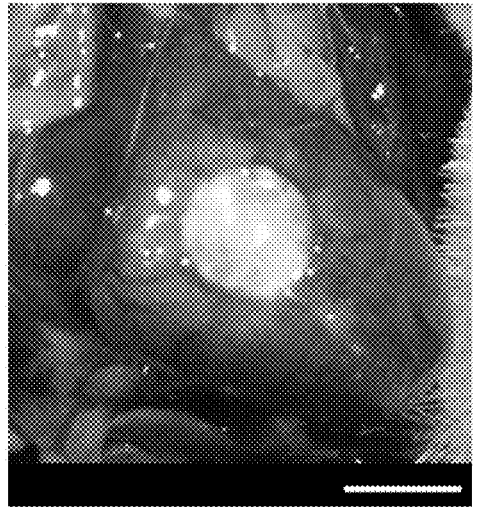

No deaths occurred during the postoperative course in either group and no gross evidence of thrombosis was present in any of the animal explants. At the time of explantation, all rat hearts exhibited minimal thoracic adhesions with no recognizable pattern of adhesive tissue present in ePTFE or PEUU implanted animals. Neither group showed any dehiscence or aneurysm formation at the implant site patch in the RVOT at each time point. FIG. 12A shows replacement of the PEUU patch with native tissue at twelve weeks after reconstruction of the RVOT. This effect was not observed with the ePTFE patch, as shown in FIG. 12B.

Figure 13A:
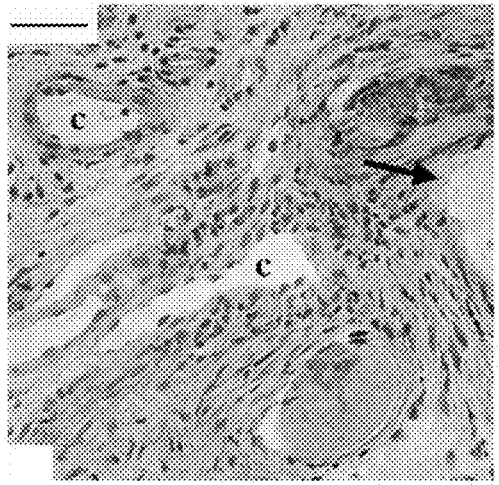
FIGS. 13A-13B are photomicrographs of hematoxylin and eosin (H&E)-stained fibrous tissue transition regions at four weeks after an implant in the free wall of the right ventricle.
Figure 13B:
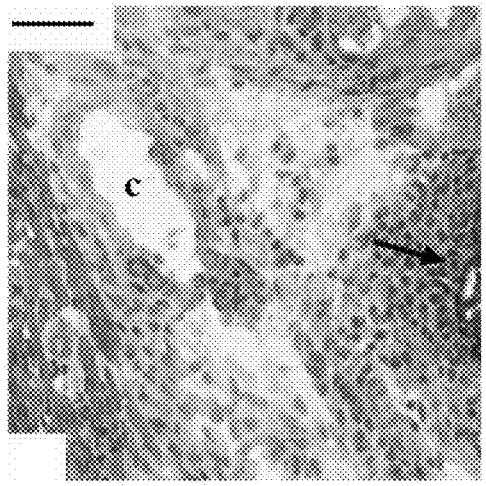
Figures 14A, 14B, 14C, 14D, 14E, 14F:
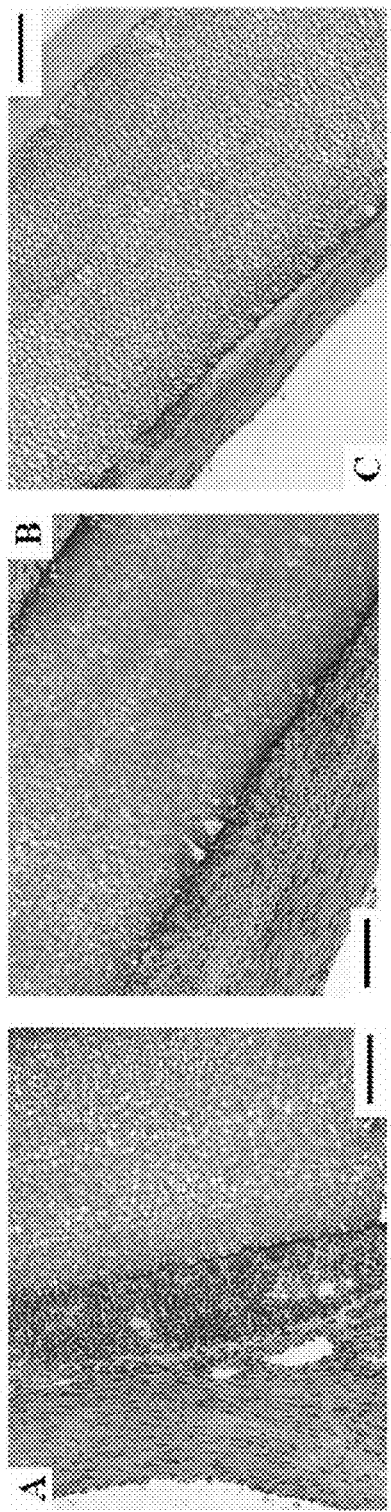
FIGS. 14A-14F are photomicrographs of hematoxylin and eosin (H&E)-stained cardiac tissue at different times after an implant in the free wall of the right ventricle.
Figure 16A:
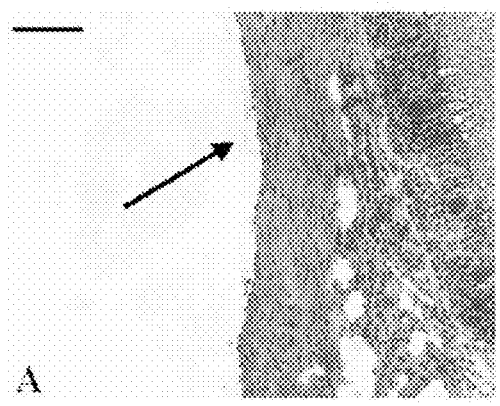
FIGS. 16A-16D are photomicrographs showing hematoxylin and eosin (H&E)-stained and immunohistochemically-stained cardiac tissue four weeks after an implant in the free wall of the right ventricle.
Figure 16B:
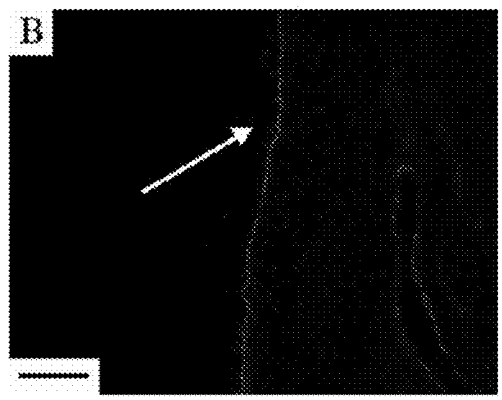
Figure 16C:
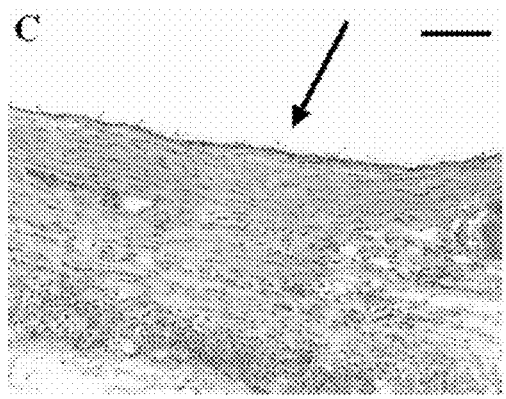
Figure 16D:
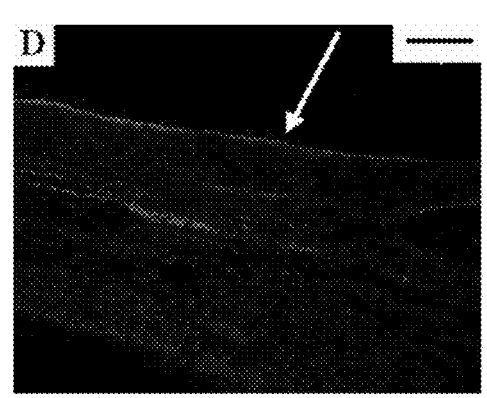

Both patches were surrounded by layered fibrous tissue at each time point. FIGS. 13A-13B shows that the fibrous capsule around both patches had capillaries mainly in the peripheral region between the patches and native right ventricular muscle. FIG. 14F shows that capillary formation was also noted in the endocardial fibrous tissue for the PEUU patched group at twelve weeks after implantation.

No cellular ingrowth was noted in e-PTFE at any time points. FIG. 14A-14C shows H&E-stained tissue with an ePTFE implant for time points of four weeks (A), eight weeks (B), and twelve weeks (C). FIGS. 15A-15C shows Masson trichrome stained-tissue with an ePTFE implant for time points of four weeks (A), eight weeks (B), and twelve weeks (C). The entire surface of the ePTFE was surrounded by a fibrous tissue with foreign body reaction composed of macrophages. The foreign body reaction was most exuberant at 4 weeks, decreased gradually, and became slight at 12 weeks.

In contrast, PEUU experienced cellular ingrowth consisting of macrophages and fibroblasts. FIG. 14D-14F shows H&E-stained tissue with a PEUU implant for time points of four weeks (D), eight weeks (E), and twelve weeks (F). FIGS. 15D-15F shows Masson trichrome-stained tissue with an ePTFE implant for time points of four weeks (D), eight weeks (E), and twelve weeks (F). Macrophage infiltration was mild throughout the course. The fibroblasts proliferated in the PEUU patch and were active in synthesizing collagen. The PEUU patches at twelve weeks were nearly completely absorbed by the putative actions of hydrolysis and phagocytosis. Histological assessment is summarized in Table 1.

TABLE 1

Tissue reaction to implanted materials

| | ePTFE | | | PEUU | | |
|---|---|---|---|---|---|---|
| | Weeks after implantation | | | | | |
| | 4 | 8 | 12 | 4 | 8 | 12 |
| Macrophages | +++ | ++ | ± | ++ | ++ | ++ |
| Neovascularization | +[a] | +[a] | +[a] | +[a] | +[a] | ++[b] |
| Cellular infiltration into material | − | − | − | + | ++ | +++ |

± to +++: sporadic to severe,
−: not present,
[a]present only in transition part,
[b]present in transition and endocardial part
Fibrous capsule formation around the patches and endothelialization of the endocardial side were present for each group.

At each time point after implantation, all the patches had complete endothelialization on the endocardial surface in the RVOT free wall. There was no thrombus observed in the endocardial surface of the patches in either group at any time point (FIG. 16).

PEUU has theoretical advantages over non-degradable materials used in reconstructive cardiovascular procedures in that it appears capable of mechanically performing early in the implant period while allowing tissue ingrowth that takes over this mechanical role by three months in this model. As with other tissue engineering approaches, complications associated with a permanent foreign body that is incapable of growth with the patient are avoided.

Example 3

Implantation of a Biodegradable Elastomeric Patch on the Left Ventricle Following Coronary Artery Occlusion to Induce an Infarction in Pig Model This example shows the feasibility of the implantation of an elastomeric, biodegradable PEUU patch onto the pig heart, the size similar to human, following sub-acute myocardial infarction.

Figure 17A:
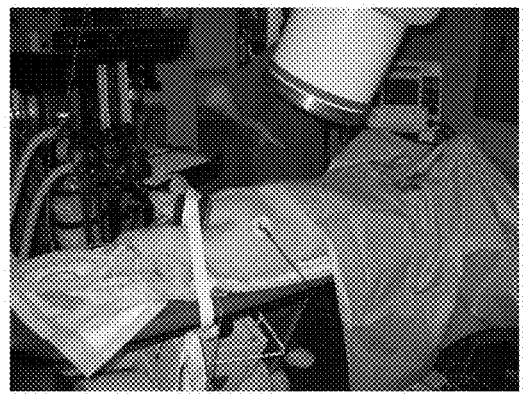
FIGS. 17A-17B show, respectively, a photograph and an echocardiogram illustrating the methods for making infarction model in pig.
Figure 17B:
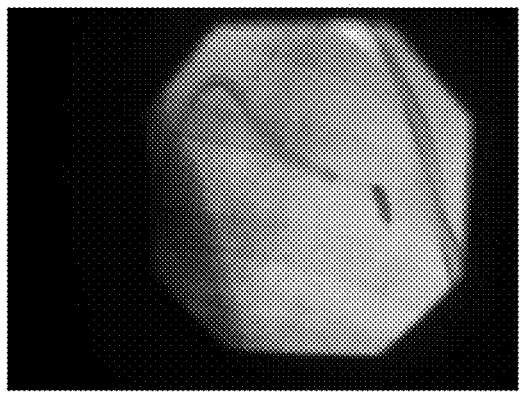

5-months old Yorkshire pigs (Wally Whippo, Enon Valley, Pa.) weighing (20-25 kg), were used in this study. The research protocol followed the National Institutes of Health guidelines for animal care and was approved by the University of Pittsburgh's Institutional Animal Care Committee. Animals were anesthetized by Ketamin (20 mg/kg), Xylazine (2 mg/kg) intramuscularly and inhalation of 3.0% isoflurane and were intubated and connected to a volume controlled mechanical ventilator. Electrocardiogram and blood pressure were continuously monitored. A peripheral IV line was inserted in an ear vein and the femoral artery was percutaneously cannulated using a 7 French arterial sheath using a modified Seldinger technique under sterile conditions (FIG. 17A). Once central vascular access was established, blood was drawn for baseline analysis of hematologic variables. The pig was given heparin 60 mg/kg intravenous bolus, and amiodarone 2 mg/kg intravenous bolus. The amiodarone continued at a drip rate of 1 mg/min continuously throughout the duration of the procedure. A cardiac catheter (AL-1, 6F, Cordis Corp., Miami, Fla., USA) was introduced through the femoral artery sheath, advanced to the ascending aorta, and inserted into the left main coronary artery using fluoroscopic guidance. A 4×8 mm PTCA balloon was inflated in the proximal left circumflex coronary artery (vessel 12 in FIG. 1, a branch of the left main coronary artery) also using fluoroscopic guidance (FIG. 17B). At 90 minutes of balloon inflation time, the balloon was deflated then removed. The guide catheter was also removed.

Figure 18A:
FIGS. 18A-18B are photographs showing PEUU patch implantation onto a pig posterior-lateral wall.
Figure 18B:
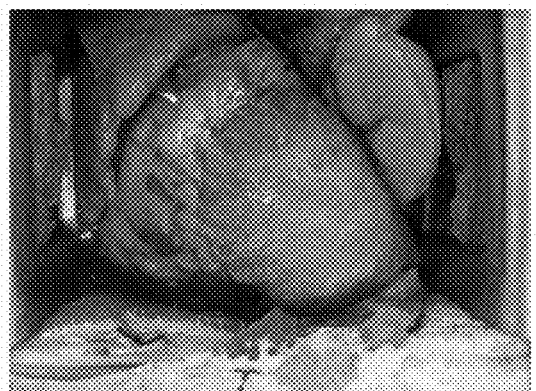

Two weeks following occlusion of the coronary artery, patch implantation surgery was performed. Before surgery, animals were screened by echocardiography for infarct size as estimated by the percentage of scar area (akinetic or dyskinetic regions) to LV free wall (LVFW) area. Animals with infarcts greater than 15% of the LVFW were chosen. The circular PEUU patch was made of a polyester urethane urea, and processed using thermally induced phase separation techniques into a patch with interconnected micropores patch. The patch possesses 91% porosity and a 91 µm average pore size. Mechanically, the patch is elastic with a tensile strength of 0.78 MPa and elongation at break of 157%. The patch material was sized to circular patches with a diameter of 5 cm diameter and thickness of 700 µm. The PEUU patches were immersed in 100% ethanol for 30 min, followed by immersion in PBS and exposure to the ultraviolet light source in a laminar flow hood for 1 hour prior to implantation. Through a left thoracotomy, infarcted posterior-lateral wall was exposed, using an "Octopus suction stabilizer" (Medtronic, Inc) (FIG. 18A). Before patch implantation, the epicardium of infarcted cardiac muscle was scraped with a surgical knife (5 cm circle size). Using 5-0 polypropylene with over-and-over sutures, the posterior-lateral infarcted myocardium was covered with PEUU patch (FIG. 18B). In the second group, each animal received a sham repair (infarction control group) in which the infarcted posterior-lateral wall was exposed via a left thoracotomy, but no patch was implanted.

Echocardiography was performed at the patch implantation (0 week), 4 weeks, and 8 weeks after PEUU patch implantation. Pigs were anesthetized with continuous inhalation of 1.5% isoflurane with 100% oxygen (2 L/min) using a nose cone. Standard transthoracic echocardiography was performed using the Acuson Sequoia C256 system (Acuson Corporation, Mountain View, Calif.) in a phased array format.

Figure 19A:
FIG. 19A-19B are photographs taken 8 weeks after implantation, indicating that there was no strong adhesion with the chest wall, suture dehiscence, infection sign, or aneurysm formation in chronic stage.
Figure 19B:
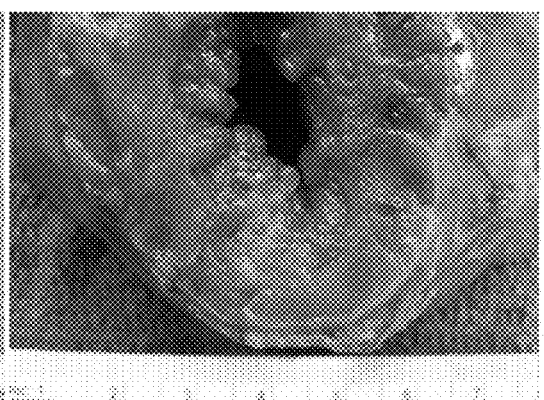

After 8 weeks implantation, a heart was harvested for histological assessment (FIGS. 19A and 19B). The implanted material was observed to have merged well into the host heart tissue without adverse effects. There were no signs of strong adhesion with the chest wall, suture dehiscence, infection, nor aneurysm formation in chronic stage.

In this study, an elastomeric, biodegradable PEUU patch could be implanted onto the pig heart, whose size is same human scale, without adverse effect. This study is ongoing.

What is claimed is:

1. A method of treating a myocardial infarct in a heart, comprising affixing a sterilized, cell-free, biodegradable, elastomeric patch to a surface of the heart to cover the infarct, thereby improving growth of muscle cells at the infarct, wherein the biodegradable elastomeric patch comprises a biodegradable, elastomeric poly(carbonate) urethane urea polymer composition.

2. The method of to claim 1, wherein the infarct is in a left ventricular region of a heart.

3. The method of claim 1, wherein the poly(carbonate) urethane urea is a poly(ester carbonate) urethane urea.

4. The method of claim 1, wherein the elastomer comprises a diamine chain extender.

5. The method of claim 4, wherein the diamine chain extender is putrescine.

6. The method of claim 4, wherein the diamine chain extender is lysine ethyl ester.

7. The method of claim 4, wherein the diamine chain extender is alanine-alanine-lysine.

8. The method of claim 1, wherein the polymer composition is functionalized with an adhesion-promoting peptide.

9. The method of claim 8, wherein the adhesion-promoting peptide comprises arginine-glycine-aspartate (RGD).

10. The method of claim 1, wherein the polymer composition has a porosity of at least 85%.

11. The method of claim 1, wherein the patch comprises a therapeutic agent.

12. The method of claim 11, wherein the therapeutic agent is one or more of basic fibroblast growth factor (bFGF), acidic fibroblast growth factor (aFGF), vascular endothelial growth factor (VEGF), pleiotrophin protein, midkine protein, anti-inflammatories, and anti-clotting agents.

13. The method of claim 11, wherein the therapeutic agent is covalently linked to a polymer in the polymer composition and is released during degradation of the patch.

14. The method of claim 11, wherein the therapeutic agent is putrescine that is covalently linked to the polymer.

15. The method of claim 1, wherein the biodegradable elastomeric patch is produced by electrospinning.

16. The method of claim 1, wherein the biodegradable elastomeric patch is produced by thermally induced phase separation.

17. The method of claim 1, wherein the biodegradable elastomeric patch is produced by solvent casting/salt leaching.

18. The method of claim 1, wherein the biodegradable, elastomeric patch is replaced by native tissue.

19. The method of claim 1, wherein the patch is mechanically supportive to the heart.

20. The method of claim 1, wherein the biodegradable poly(carbonate) urethane urea polymer composition has a breaking strain range of from 100% to 900%, a tensile strength of from 10 kPa to 30 MPa, and/or an initial modulus of from 10 kPA to 100 MPa.

21. The method of claim 20, wherein the biodegradable poly(carbonate) urethane urea polymer composition has a tensile strength of from 8 MPa to 20 MPa.

22. The method of claim 1, wherein the poly(carbonate) urethane urea polymer composition is substantially degraded within twelve weeks of being affixed to the heart.

23. The method of claim 1, wherein the biodegradable patch exhibits a degradation profile such that the patch is more than 50% degraded after twelve weeks in vivo.

* * * * *

UNITED STATES PATENT AND TRADEMARK OFFICE
CERTIFICATE OF CORRECTION

PATENT NO.        : 9,968,714 B2
APPLICATION NO.   : 14/597520
DATED             : May 15, 2018
INVENTOR(S)       : Kazuro Lee Fujimoto et al.

It is certified that error appears in the above-identified patent and that said Letters Patent is hereby corrected as shown below:

On the Title Page

Column 1, (*) Notice, Line 3, after "0 days." delete "days."

In the Claims

Column 23, Line 30, Claim 2, after "of" delete "to"

Signed and Sealed this
Twenty-first Day of August, 2018

Andrei Iancu
*Director of the United States Patent and Trademark Office*